United States Patent
Morad et al.

(10) Patent No.: US 10,160,967 B2
(45) Date of Patent: Dec. 25, 2018

(54) METHODS AND COMPOSITIONS FOR IDENTIFYING A PEPTIDE HAVING AN INTERMOLECULAR INTERACTION WITH A TARGET OF INTEREST

(71) Applicant: AEBI LTD., Ness Zionna (IL)

(72) Inventors: Ilan Morad, Ness Zionna (IL); Hanan Itzhaki, Ness Zionna (IL)

(73) Assignee: AEBi Ltd., Nes Zionna (IL)

( * ) Notice: Subject to any disclaimer, the term of this patent is extended or adjusted under 35 U.S.C. 154(b) by 416 days.

(21) Appl. No.: 14/923,855

(22) Filed: Oct. 27, 2015

(65) Prior Publication Data

US 2016/0046929 A1 Feb. 18, 2016

Related U.S. Application Data

(63) Continuation of application No. 11/989,203, filed as application No. PCT/IL2006/000815 on Jul. 12, 2006, now abandoned.
(Continued)

(51) Int. Cl.
  *C12N 15/10* (2006.01)
  *C40B 10/00* (2006.01)
  (Continued)

(52) U.S. Cl.
  CPC ..... *C12N 15/1037* (2013.01); *C12N 15/1058* (2013.01); *C40B 10/00* (2013.01);
  (Continued)

(58) Field of Classification Search
  CPC ............ C07K 2319/50; C07K 2319/70; C12N 15/1037; C12N 15/1058; C40B 10/00;
  (Continued)

(56) References Cited

U.S. PATENT DOCUMENTS 4,879,236 A 11/1989 Smith et al.
5,871,986 A 2/1999 Boyce
(Continued)

FOREIGN PATENT DOCUMENTS

WO 2005/007822 A2 1/2005

OTHER PUBLICATIONS

Altschul et al., "Basic Local Alignment Search Tool," J. Mol. Biol., 215:403-410 (1990).
(Continued)

*Primary Examiner* — Jeremy C Flinders
(74) *Attorney, Agent, or Firm* — Winston & Strawn LLP

(57) ABSTRACT

A system of a recombinant bacteriophage library and a target of interest complex, wherein the recombinant bacteriophage peptide library includes a plurality of peptides expressed on the surface of recombinant bacteriophages wherein each recombinant bacteriophage includes (a) a pill protein; wherein each pill protein includes (b) a peptide or polypeptide involved in an intermolecular interaction, which differs by at least one amino acid from other peptides or polypeptides in the library; and (c) a modified protease cleavage site proximal to the peptide, wherein the modified protease cleavage site is the same in each bacteriophage, the modified cleavage site having a reduced binding affinity to a protease, as compared to a non-modified cleavage site, and wherein the target of interest complex includes a protease, a flexible linker attached to the protease, and a target of interest attached to the flexible linker, wherein the target of interest participates in an intermolecular interaction.

8 Claims, 7 Drawing Sheets

Specification includes a Sequence Listing.

M13 bacteriophage pIII protein domains
N1 - forms a complex with the C-terminal of bacterial TolA at late stages of infection
N2 - interacts with bacterial F pilus
CT - anchors pIII to the phage coat

Related U.S. Application Data

(60) Provisional application No. 60/701,092, filed on Jul. 21, 2005.

(51) Int. Cl.
    *C40B 40/02*     (2006.01)
    *G01N 33/50*     (2006.01)
    *G01N 33/569*     (2006.01)

(52) U.S. Cl.
    CPC ......... *C40B 40/02* (2013.01); *G01N 33/5023* (2013.01); *G01N 33/56983* (2013.01); *C07K 2319/50* (2013.01); *C07K 2319/70* (2013.01); *G01N 2333/95* (2013.01)

(58) Field of Classification Search
    CPC ................ C40B 40/02; G01N 33/5023; G01N 33/56983; G01N 2333/95
    See application file for complete search history.

(56) References Cited

U.S. PATENT DOCUMENTS

| | | |
|---|---|---|
| 6,683,170 B2 | 1/2004 | Curiel et al. |
| 6,743,893 B2 | 6/2004 | Engler et al. |
| 7,442,159 B1 | 10/2008 | Riechmann et al. |
| 2003/0186329 A1 | 10/2003 | Madison et al. |
| 2005/0100934 A1 | 5/2005 | Lee et al. |

OTHER PUBLICATIONS

Altschul et al., "Gapped BLAST and PSI-BLAST: a new generation of protein database search programs," Nucleic Acids Research, 25(17):3389-3402 (1997).

Jung et al., "Selectively infective phage (SIP) technology: scope and limitations," Journal of Immunological Methods, 231:93-104 (1999).

Kinoh et al., "Generation of a recombinant Sendai virus that is selectively activated and lyses human tumor cells expressing matrix metalloproteinases," Gene Therapy, 11:1137-1145 (2004).

Skolnik et al., "Cloning of PI3 Kinase—Associated p85 Utilizing a Novel Method for Expression/Cloning of Target Proteins for Receptor Tyrosine Kinases," Cell, 65:83-90 (1991).

U.S. Appl. No. 11/989,203, Restriction Requirement, dated Mar. 9, 2010.

U.S. Appl. No. 11/989,203, Non-Final Office Action, dated Nov. 12, 2010.

U.S. Appl. No. 11/989,203, Final Office Action, dated Apr. 4, 2011.

U.S. Appl. No. 11/989,203, Advisory Action, dated Jun. 3, 2011.

U.S. Appl. No. 11/989,203, Non-Final Office Action, dated Jan. 13, 2015.

U.S. Appl. No. 11/989,203, Final Office Action, dated Aug. 3, 2015.

mUb- modified Ubiquitin, which has a reduced affinity to its protease, UBP.
Leu-Zip1 and LeuZip2 – two interacting halves of the leucine zipper peptide

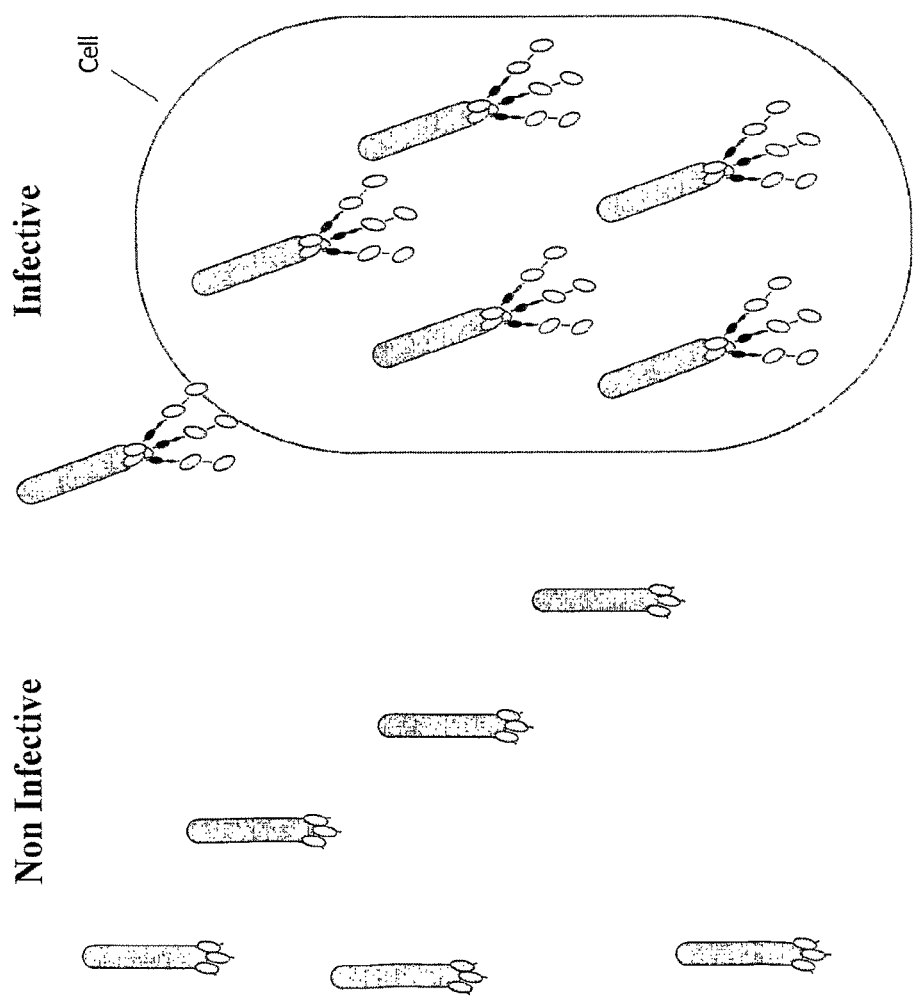

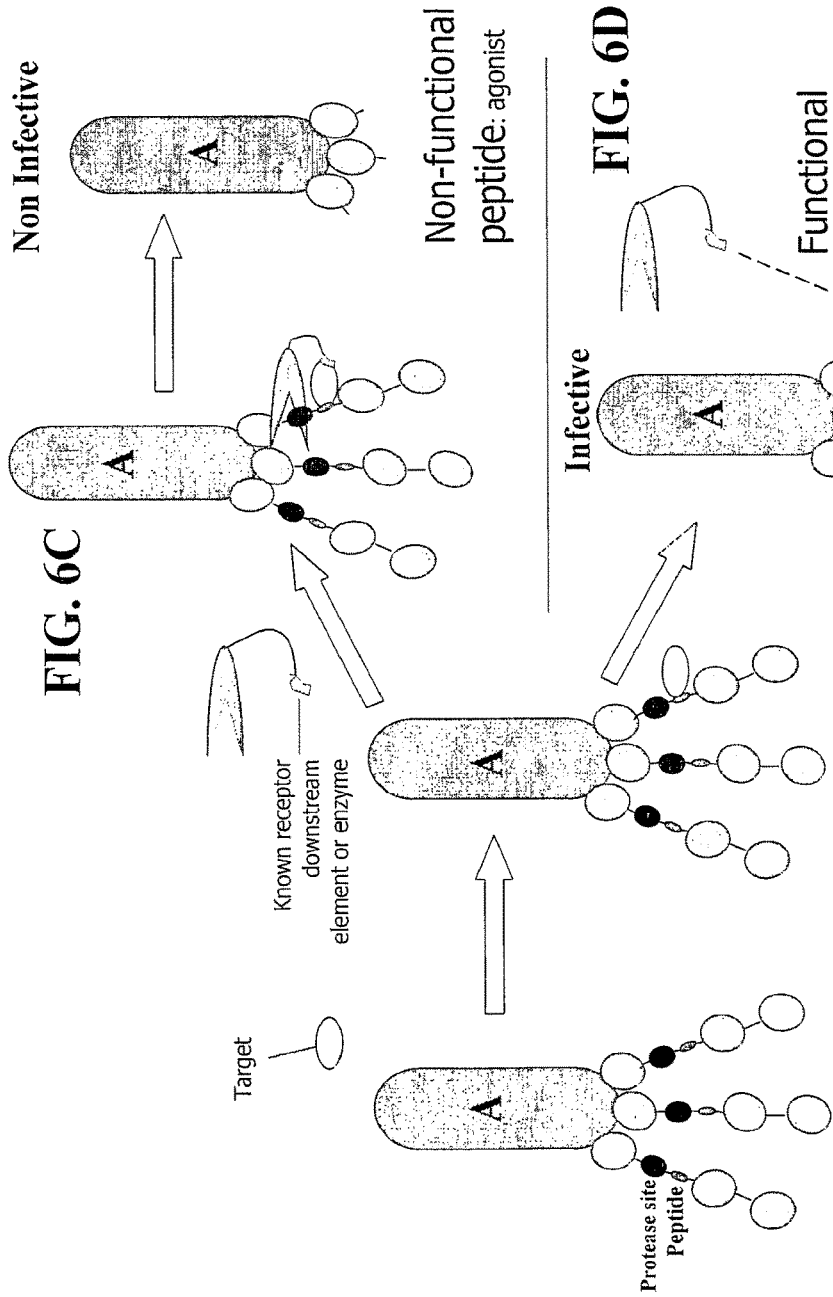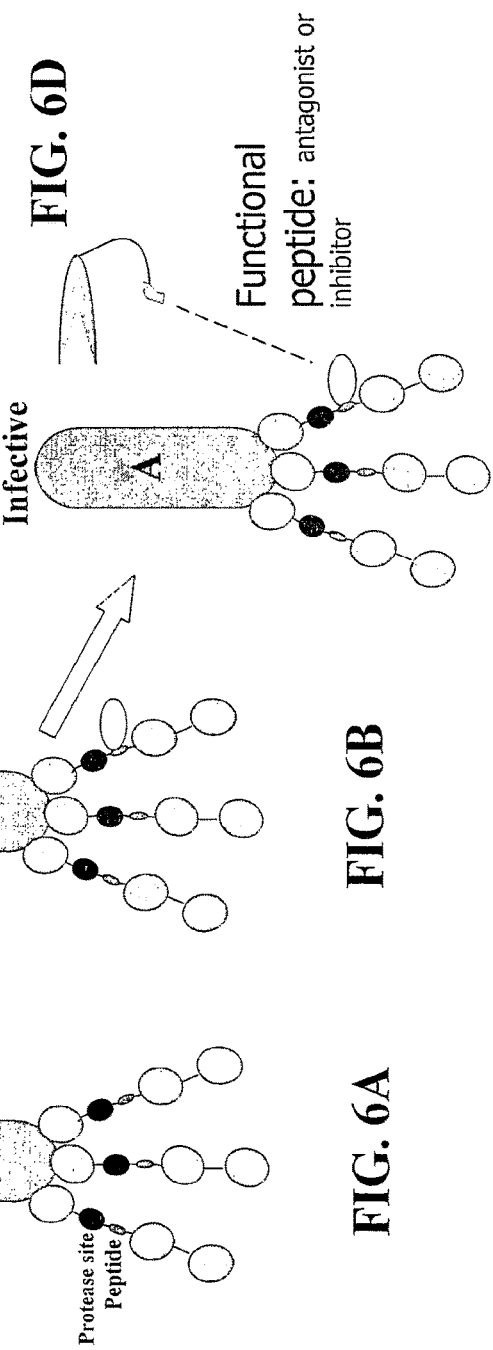

METHODS AND COMPOSITIONS FOR IDENTIFYING A PEPTIDE HAVING AN INTERMOLECULAR INTERACTION WITH A TARGET OF INTEREST

CROSS-REFERENCE TO RELATED APPLICATIONS

This application is a continuation of U.S. application Ser. No. 11/989,203 filed on Jan. 22, 2008, which is the 371 filing of International application no. PCT/IL2006/000815 filed on Jul. 12, 2006, which claims the benefit of U.S. provisional application No. 60/701,092 filed on Jul. 21, 2005, the entire content of each of which is incorporated herein by reference thereto.

FIELD OF THE INVENTION

This invention is directed to a method of identifying a polypeptide having an intermolecular interaction with a target of interest and functional features thereof.

BACKGROUND OF THE INVENTION

Phage display has become a powerful method for screening populations of peptide or polypeptides, mutated proteins, and cDNAs for members that have affinity to target molecules of interest. It is possible to generate many different recombinants from which one or more clones can be selected with affinity to antigens, antibodies, cell surface receptors, protein chaperones, DNA, metal ions, etc. Screening libraries are versatile because the displayed elements are expressed on the surface of the virus as capsid-fusion proteins. The most important consequence of this arrangement is that there is a physical linkage between phenotype and genotype. There are several other advantages as well: 1) virus particles which have been isolated from libraries by affinity selection can be regenerated by simple bacterial infection and 2) the primary structure of the displayed binding peptide or protein can be easily deduced by DNA sequencing of the cloned segment in the viral genome.

Synthetic oligonucleotides that are fixed in length, but with multiple unspecified codons can be cloned into genes III, VI, or VIII of bacteriophage Ml 3 where they are expressed on the capsid fusion protein. The libraries, often referred to as random peptide libraries, can be screened for binding to target molecules of interest.

Most vital cellular processes are regulated by the transmission of signals wherein such signal transduction is likely mediated by protein-protein interactions involving modular domains within the signaling proteins.

Methods for isolating partner proteins involved in protein-protein interactions have generally focused on finding a ligand to a characterized protein. Such approaches have included using anti-idiotypic antibodies that mimic the known protein to screen cDNA expression libraries for a binding ligand (Jerne, 1974, Ann. Immunol. (Inst. Pasteur) 125c:373-389; Sudol, 1994, Oncogene 9:2145-2152). Skolnick et al. (1991, Cell 65:83-90) isolated a binding partner for $PI_3$-kinase by screening a cDNA expression library with the $^{32}P$-labeled tyrosine phosphorylated carboxyl terminus of the epidermal growth factor receptor (EGFR). While current methods provide for the identification and isolation of a peptides having an intermolecular interaction with a target of interest, functional analysis of the screening steps is currently lacking.

SUMMARY OF THE INVENTION

This invention provides, in one embodiment, a recombinant virus comprising a protein or protein fragment, comprising segments which are involved in viral attachment, infection or a combination thereof, a peptide or polypeptide involved in an intermolecular interaction, and a modified cleavage site that is proximal to said peptide and to said segments of said protein, wherein said cleavage site is modified such that a compound mediating cleavage has a reduced binding affinity for it.

In another embodiment, this invention provides a recombinant virus library wherein each virus comprises a protein or protein fragment, comprising segments which are involved in viral attachment, infection or a combination thereof, a peptide or polypeptide which differs by at least a single amino acid from another peptide or polypeptide in said library, and a modified cleavage site that is proximal to said peptide and to said segments of said protein, wherein said cleavage site is modified such that a compound mediating cleavage has a reduced binding affinity for said cleavage site as compared to a non-modified cleavage site.

In another embodiment, the invention provides a target of interest complex comprising a protease, a target of interest involved in an intermolecular interaction, and a flexible linker that attaches the protease and target of interest.

In another embodiment, this invention provides a method of identifying a peptide or polypeptide having an intermolecular interaction with a target of interest comprising the steps of: (a) contacting a recombinant virus library as described hereinabove with a plurality of complexes as described hereinabove; (b) contacting said library with a plurality of cells; (c) isolating viruses that did not infect said cells; (d) providing infectious clones of isolated viruses by amplifying and expressing the genomes of said isolated viruses; (e) repeating the above steps; and (f) identifying peptides expressed by said viruses whereby intermolecular interactions between said target of interest and a peptide expressed by said recombinant virus result in said protease being in close proximity to said cleavage site, resulting in cleavage of said protein or protein fragment, comprising segments which are involved in viral attachment to, infection of, or a combination thereof of cells, and prevention of entry of a virus that had comprised a peptide involved in intermolecular interactions into said cells.

In another embodiment, this invention provides a kit for identifying a peptide or polypeptide involved in an intermolecular interaction with a target of interest comprising a recombinant virus peptide library as described hereinabove, a target of interest complex as described hereinabove, and cells that are susceptible to viral attachment, infection or a combination thereof.

In another embodiment, this invention provides a method for identifying an agonistic or antagonistic feature of a peptide or polypeptide that has an inter molecular interaction with a receptor of interest comprising the steps of: (a) contacting the recombinant virus library as described hereinabove with a plurality of complexes as described hereinabove, wherein the target of interest is a receptor; (b) contacting said recombinant virus library of step (a) with cells; (c) isolating viruses in (b) which have not infected said cells; (d) providing infectious clones of first isolated viruses of (c) by amplifying and expressing the genomes of said first isolated viruses; (e) contacting infectious clones of viruses of step (c) with the receptor of interest, wherein said receptor is not attached to a protease; (f) contacting the viruses of step (e) with a protein attached to a protease via a flexible linker, wherein said protein is involved in the downstream signal transduction pathway of said receptor of interest; (g) contacting the viruses of step (f) with cells; (h) separating viruses in (g) that have not infected said cells from viruses which have infected cells; (i) providing infectious clones of second isolated viruses of step (h) by amplifying and expressing the genomes of said second isolated viruses; (j) repeating steps (a)-(i); and (k) identifying peptides expressed by the viruses in step (h), whereby viruses which have not infected said cells in (h) express a peptide which has agonistic activity for said receptor of interest, and viruses which have infected said cells in (h) express a peptide which has antagonistic activity for said receptor.

In another embodiment, this invention provides a method for identifying a peptide or polypeptide that inhibits an enzyme of interest comprising the steps of: (a) contacting the recombinant virus library as described hereinabove with a plurality of complexes as described hereinabove, wherein the target of interest is an enzyme; (b) contacting said recombinant virus library of step (a) with cells; (c) isolating viruses in (b) which have not infected said cells; (d) providing infectious clones of first isolated viruses of (c) by amplifying and expressing the genomes of said first isolated viruses; (e) contacting infectious clones of viruses of step (c) with the enzyme of interest, wherein said enzyme is not attached to a protease; (f) contacting the viruses of step (e) with a substrate of the enzyme attached to a protease via a flexible linker; (g) contacting the viruses of step (f) with cells; (h) separating viruses in (g) which have not infected said cells from viruses which have infected cells; (i) providing infectious clones of second isolated viruses of step (i) by amplifying and expressing the genomes of said second isolated viruses; (j) repeating steps (a)-(i); and (k) identifying peptides expressed by the viruses in step (h), whereby viruses which have not infected said cells in (h) express a peptide which does not affect said enzyme of interest, and viruses which have infected said cells in (h) express a peptide which inhibits said enzyme.

BRIEF DESCRIPTION OF THE DRAWINGS

FIG. 4 is an illustration in one embodiment of the method of incubating infective and non-infective SoIP with bacteria. Only infective SoIP are able to enter the bacterial cell. After incubation, bacterial cells containing infecting SoIP are removed, and non-infective SoIP remain in the medium.

FIGS. 6A-6D are an illustration of an embodiment of the present invention in which the invention can distinguish between functional and non-functional peptides or polypeptides using the SoIP assay. Functional proteins may be further categorized as antagonist, agonist, and/or inhibitor. Recombinant viruses that comprise a peptide from the peptide library (referred to as "Peptide") that demonstrates binding to a target protein of interest are incubated with the target (6A). Next, a fusion protein comprising a protease fused to a known target's ligand is added to the incubation mixture comprising the recombinant virus (6B). The ligand can be a downstream element, in case the target is a receptor, or an enzyme, that works on the target. The peptide can either facilitate the binding of the target and its ligand, or not. In case the peptide facilitates binding of the target and its ligand, the protease and the modified protease site are brought into close proximity. This will lead to the cleavage of the pIII protein, which will render the recombinant virus non-infective (6C). If the peptide inhibits the binding of the target and its ligand, the pIII protein will not be cleaved and the recombinant virus will remain infective (6D).

DETAILED DESCRIPTION OF THE INVENTION

Figure 1:
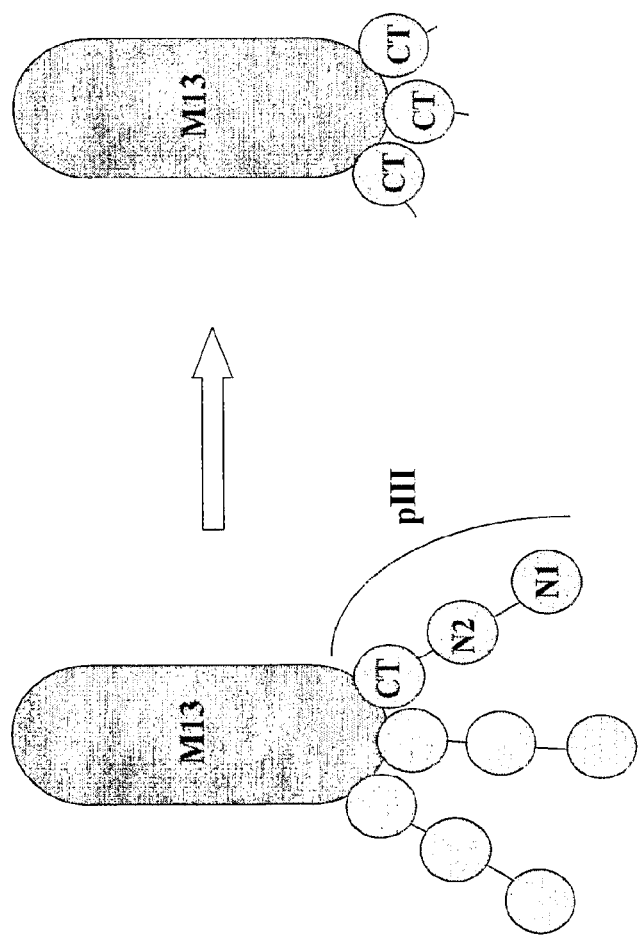
FIG. 1 is an illustration of the conversion, in one embodiment, of an infective (A) to a non-infective (B) via cleavage of the N1 and N2 domains from the CT domain of the phage minor coat gene 3 (pIII) protein of the M13 bacteriophage, which is attached to the bacteriophage capsid.

This invention provides a recombinant virus and a recombinant virus library and its use in identifying interacting polypeptides, which may find application in diagnostics and/or therapeutics.

Recombinant Virus

In one embodiment, a recombinant virus of this invention comprises: a protein or protein fragment, comprising segments which are involved in viral attachment to, infection of or a combination thereof of a host cell; a peptide or polypeptide involved in an intermolecular interaction; and a modified cleavage site that is proximal to said peptide and to said segments of said protein, wherein the cleavage site is modified such that a compound mediating cleavage has a reduced binding affinity for said cleavage site, as compared to a non-modified cleavage site.

In one embodiment, viruses of the present invention may infect mammalian, insect, plant, bacteria cells or a combination thereof. In one embodiment, a virus of the present invention may be a bacteriophage. In another embodiment, a virus of the present invention may be a filamentous bacteriophage. In another embodiment, a virus of the present invention may be M13. In another embodiment, it may be lambda phage, fd, f1, or T4. In another embodiment, a virus of the present invention may be Mycobacteria phage. In one embodiment, it might be Mycobacteria phage D29, Mycobacteriophage Bethlehem, Mycobacteriophage U2, *Mycobacterium* phage L5, or *Mycobacterium* phage TM4.

Bacteriophage (phage) are viruses that have a specific affinity for and infect bacteria. Phages consist of a protein coat or capsid enclosing the genetic material (DNA or RNA) that is injected into a bacterium upon infection. Phages may be lytic or temperate. Lytic phages lyse, or break apart, the host cell, while temperate phages integrate their DNA into that of the host (lysogeny). In the case of lytic phages, all synthesis of host DNA, RNA and proteins ceases, and the phage genome is used to direct the synthesis of phage nucleic acids and proteins using the host's transcriptional and translational apparatus. These phage components then self assemble to form new phage particles. The synthesis of a phage lysozyme leads to rupture of the bacterial cell wall releasing typically 100-200 phage progeny. The temperate phages, such as lambda, may also show this lytic cycle when they infect a cell, but more frequently they induce lysogeny. Examples of bacteriophages that attack *Escherichia coli* are lambda phage and the T even phages, T2, T4 and T6.

In another embodiment, viruses can include any desired virus, as will be recognized by those of skill in the art, including but not limited to Adenoviruses, Herpesviruses, Poxviruses, Parvoviruses, Reoviruses, Birnaviruses, Picornaviruses, Togaviruses, Orthomyxoviruses, Rhabdoviruses, Retroviruses, Hepadnaviruses, Enterovirus, Cardiovirus, Rhinovirus, Apthovirus, Hepatovirus, etc. In one embodiment, viruses are lysogenic, while in another embodiment, viruses are temperate.

In one embodiment, the term "recombinant virus" refers to viruses that are engineered to express foreign or modified protein or proteins, which are not natively expressed in that virus. At least one protein or protein fragment is expressed by the recombinant virus.

In another embodiment, the virus can be modified in any of various ways known in the art, such as to introduce temperature sensitivity, to introduce a reporter gene, to be rendered replication-deficient, or to eliminate other viral genes. Methods of such modifications are standard in the art. In one embodiment, the virus is modified to express the peptide on the surface of the virus, as by engineering the virus genome to encode a fusion protein for a coat protein and the peptide. In one embodiment, the present invention further provides a recombinant virus comprising a selectable marker or label such that the label can be directly detected. The selectable marker can be any selectable marker, which is known in the art, such as antibiotic resistance protein, for example, without being limited, ampicillin. The selectable marker can be also used for deletion mutants counter selection, when there is a need to select cells that are infected by virus that did not lose essential genes.

In one embodiment, the term "protein or protein fragment" refers to a molecule comprised of amino acid residues joined by peptide (i.e., amide) bonds and includes peptides, polypeptides, and proteins. In another embodiment, "protein or protein fragment" refers to a protein or protein fragment comprising segments which are involved in viral attachment, infection, or a combination thereof. In one embodiment, the term "segment" refers to a sequence of amino acids of any length with functional or structural homology to proteins known to mediate viral attachment, infection, or a combination thereof. In one embodiment, a "tail" refers to a protein involved in viral attachment, infection, or a combination thereof.

In one embodiment, a segment of said protein or protein fragment mediates attachment. In one embodiment, the term "attachment" refers to a physical connection between a virus and a host cell. In the process of viral infection, a virus attaches to a host cell in order to enter or penetrate it. Many viruses comprise a protein expressed on its surface, sometimes referred to as an "antireceptor" which binds to a constituent of the cell surface of a potential host cell, sometimes referred to as a "receptor." In one embodiment, the proteins or protein segments involved in viral attachment comprise the pIII protein. In another embodiment, the protein or protein segments comprise the PVIII protein. In one embodiment, the proteins or protein segments involved in viral attachment comprise the N2 domain of the pIII protein (a.k.a. Coat Protein A) of filamentous bacteriophage (M13, fd, f1, I2-2, If1, Ike, Pf1), the A protein of Bacteriophage fr, GA, or MS2, the Gp38 protein (a.k.a. receptor recognizing protein) of Bacteriophage AR1, K3, M1, Ox2, or T2, the J protein of Bacteriophage lambda, φx174, α3, or G4, and others, known to one skilled in the art. In another embodiment, the proteins or protein segments involved in viral attachment comprise hemagglutinin of influenza virus, gp120 envelope glycoprotein of HIV or segments thereof, and others, known to one skilled in the art.

In one embodiment, a segment of said protein or protein fragment mediates infection. In one embodiment, the term "infection", "entry," "fusion" and "penetration" refer to fusion of a virus with the membrane of a host cell to allow the passage of genetic material or a complete virus into the host cell. Some viruses comprise a protein or a protein segment that is involved in cell entry. In one embodiment, the proteins or protein segments involved in infection comprise the pIII protein. In another embodiment, the protein or protein segments comprise the PVIII protein. In one embodiment, a protein or a protein segment that is involved in infection is the N1 domain of the pIII protein of filamentous bacteriophage. In another embodiment, a protein or a protein segment that is involved in infection is the gp41 of HIV-1, while in another embodiment, it's the V3 domain or other segments of the gp120 of HIV-1.

In one embodiment, the protein or protein fragment comprising segments involved in viral attachment, infection or a combination thereof are structural or functional homologs of those mentioned hereinabove. In another embodiment, the segment involved in viral attachment, infection or a combination thereof are synthetically constructed using methods well known in the art.

In one embodiment, two protein fragments of a single protein mediate mediate attachment and infection. In another embodiment, a single protein or protein fragment mediates both attachment and infection. In another embodiment, two protein fragments of two distinct proteins mediate attachment and infection. In another embodiment, two protein fragments of two distinct proteins mediate attachment and infection. In another embodiment, two distinct proteins mediate attachment and infection.

Non-Endogenous Peptides

In one embodiment, each recombinant virus of the present invention comprises a peptide involved in at least one intermolecular interaction. In one embodiment, the term "polypeptide" or "peptide" refers to a molecule comprised of amino acid residues joined by peptide (i.e., amide) bonds and includes peptides, polypeptides, and proteins. Hence, in one embodiment, the polypeptides of this invention may have single or multiple chains of covalently linked amino acids and may further contain intrachain or interchain linkages comprised of disulfide bonds. In one embodiment, some polypeptides may also form a subunit of a multiunit macromolecular complex. In one embodiment, the polypeptides can be expected to possess conformational preferences and to exhibit a three-dimensional structure. Both the conformational preferences and the three-dimensional structure will usually be defined by the polypeptide's primary (i.e., amino acid) sequence and/or the presence (or absence) of disulfide bonds or other covalent or non-covalent intrachain or interchain interactions. In another embodiment, the polypeptides do not possess conformational preferences or exhibit a three-dimensional structure.

In one embodiment, the terms "peptides", "polypeptides", "plurality of peptides" or "plurality of polypeptides" can be used interchangeably and refer to more than one peptide or polypeptide.

The polypeptide of the present invention can be of any size. As can be expected, the polypeptides can exhibit a wide variety of molecular weights, some exceeding 150 to 200 kilodaltons (kD). Typically, the polypeptides may have a molecular weight ranging from about 5,000 to about 100,000 daltons. Still others may fall in a narrower range, for example, about 10,000 to about 75,000 daltons, or about 20,000 to about 50,000 daltons. In an alternative embodiment, the polypeptides of the present invention may be 1-250 amino acid residues long. In another embodiment, the polypeptides of the present invention may be 10-200 amino acid residues long. In an alternative embodiment, the polypeptides of the present invention may be 50-100 amino acid residues long. In an alternative embodiment, the polypeptides of the present invention may be 1-250 amino acid residues long. In an alternative embodiment, the polypeptides of the present invention may be 1-250 amino acid residues long.

The peptides or polypeptides, or the DNA sequences encoding same, may be obtained from a variety of natural or unnatural sources, such as a prokaryotic or a eukaryotic cell. In one embodiment, the source cell may be wild type, recombinant, or mutant. In another embodiment, the plurality of peptides or polypeptides may be endogenous to microorganisms, such as bacteria, yeast, or fungi, to a virus, to an animal (including mammals, invertebrates, reptiles, birds, and insects) or to a plant cell.

In another embodiment, the peptides or polypeptides may be obtained from more specific sources, such as the surface coat of a virion particle, a particular cell lysate, a tissue extract, or they may be restricted to those polypeptides that are expressed on the surface of a cell membrane.

In another embodiment, the peptide or polypeptide is derived from a particular cell or tissue type, developmental stage or disease condition or stage. In one embodiment, the disease condition or stage is cancer, in another embodiment, it's an infection, in another embodiment, it's an HIV infection, in another embodiment, it's a developmental disorder, while in another embodiment, it's a metabolic disorder.

In one embodiment, the peptide or polypeptide is obtained from a peptide or polypeptide library as is described hereinbelow. In another embodiment, it's created synthetically and inserted into a vector as is well known in the art. In one embodiment, the term "vector" is used to refer to a carrier nucleic acid molecule into which a nucleic acid sequence can be inserted for introduction into a cell where it can be replicated.

In one embodiment, the peptide or polypeptide is expressed on the external surface of the virus. In another embodiment, the peptide or polypeptide is not the most terminal peptide on a protein or recombinant protein expressed on the external surface of the virus. In one embodiment, "terminal" refers to the absolute end of a protein or polypeptide. In one embodiment, the peptide or polypeptide is not at the 3' end of a protein or recombinant protein expressed on the external surface of the virus, while in another embodiment, it is not at 5' end of a protein or recombinant protein. In one embodiment, the peptide or polypeptide is not among the last 50 amino acids of a protein or recombinant protein. In another embodiment, the peptide or polypeptide is not among the last 100 amino acids of a protein or recombinant protein. In another embodiment, the peptide or polypeptide is not among the last 500 amino acids of a protein or recombinant protein.

In another embodiment, the peptide or polypeptide is connected to the proximal segments of the protein or protein fragment involved in viral attachment, infection, or a combination thereof via a flexible linker. In one embodiment, the linker is G1 or G2 of the protein pIII of M13. In another embodiment, the flexible linker is a (Gly-Gly-Gly-Ser-)n (SEQ ID No. 1) synthetic linker. In another embodiment, any other flexible linker could be used.

In another embodiment, the peptides or polypeptides are agonists. In another embodiment, the peptides or polypeptides are antagonists. In another embodiment, the peptides or polypeptides are antigens. In another embodiment, the peptides or polypeptides are enzymes. In another embodiment, the peptides or polypeptides are activators of enzymes or other substrates. In another embodiment, the peptides or polypeptides are inhibitors of enzymes or other substrates. In another embodiment, the peptides or polypeptides are hormones. In another embodiment, the peptides or polypeptides are regulatory proteins. Regulatory proteins command the numerous interactions that govern the expression and replication of genes, the performance of enzymes, the interplay between cells and their environment, and many other manifestations. In another embodiment, the peptides or polypeptides are cytoskeletal proteins. Cytoskeletal proteins form a flexible framework for the cell, provide attachment points for organelles and formed bodies, and make communication between parts of the cell possible. In another embodiment, the peptides or polypeptides are toxins. In another embodiment, the peptides or polypeptides are functional fragments of agonists, antagonists, antigens, enzymes, enzyme activators, enzyme inhibitors, enzyme substrates, hormones, regulatory proteins, cytoskeletal proteins, or toxins. "Functional fragments" are meant to indicate a portion of the peptide or polypeptide which is capable of performing one or more of the functions of the peptide or polypeptide, even in the absence of the remainder of the peptide or polypeptide. In one embodiment, the functional fragment is sufficient to mediate an intermolecular interaction with a target of interest.

In an alternative embodiment, the peptide binds DNA or RNA or a fragment thereof. In one embodiment, the DNA or RNA binding peptide may be any of the many known in the art including, but not limited to: Zinc finger proteins such as Beta-beta-alpha zinc finger proteins, Nuclear receptor proteins, Loop-sheet-helix type protein, and GAL4 type protein; the Helix-turn-helix proteins such as Cro and repressor proteins, Lad purine repressor proteins (PurR), Fold restriction endonuclease (DNA-recognition region), Gamma-delta recombinase protein (C-terminal domain), Hin recombinase protein, Trp repressor protein, Diptheria tox repressor, Catabolite gene activator proteins (CAP), Homeodomain proteins, RAP1 protein, Prd paired protein, Tc3 transposase protein, TFIIB family, Interferon regulatory factor, Transcription factor family, and ETS domain family bacteriophage; and the Leucine zipper proteins such as Basic zipper proteins and Zipper-type proteins (helix-loop-helix). In another embodiment, the DNA or RNA binding peptide may be other alpha-helix proteins such as Cre recombinase family, Papillomavirus-1 E2 protein, Histone family, Ebna1 nuclear protein family, Skn-1 transcription factor, High mobility group family, and MADS box family; Beta-sheet proteins such as TATA Box-Binding Proteins; Beta-hairpin/ribbon proteins such as Met repressor protein, Tus replication terminator protein, Integration host factor protein, Hyperthermophile DNA binding protein, Arc repressor, Transcription factor T domain; and other protein families such as Rel homology region proteins and Stat family. In another embodiment, the DNA or RNA binding peptide may be enzymes such as Methyl transferase proteins, PvuII Endonuclease protein, Endonuclease V protein, EcoRV Endonuclease family, BamHI Endonuclease family, EcoRI endonuclease family, DNA mismatch endonuclease, DNA polymerase I protein, DNA polymerase T7, Dnase I proteins, DNA polymerase beta proteins, Uraci-DNA glycosylase, Methyladenine-DNA glycosylase, Homing endonuclease, and Topoisomerase I or viral proteins such as HIV reverse transcriptase.

In another embodiment, the peptide or polypeptide is a transcriptional or translational activator or a fragment thereof. In another embodiment, the peptide or polypeptide is a transcriptional or translational repressor or a fragment thereof. In another embodiment, the peptide or polypeptide is a receptor or a fragment thereof. In another embodiment, the peptide or polypeptide is an organic molecule, inorganic compound, or organometallic compound or a fragment thereof.

In one embodiment, the peptide or polypeptide may represent a cognate peptide of any of the peptides or polypeptides described hereinabove. A "cognate" peptide is any peptide that interacts and/or binds to another molecule.

The peptide or polypeptide identified by this invention can be in another embodiment, a potential drug candidate or a "lead" compound.

Compounds that pass an initial in vitro screening test, such as the methods of the present invention, are known as "lead" compounds. These lead compounds are then put through further testing, including, eventually, in vivo testing in animals and humans, from which the promise shown by the lead compounds in the original in vitro tests is either, confirmed or refuted. See Remington's Pharmaceutical Sciences, 1990, A. R. Gennaro, ed., Chapter 8, pages 60-62, Mack Publishing Co., Easton, Pa.; Ecker and Crooke, 1995, Bio/Technology 13:351-360.

Intermolecular Interaction

In one embodiment, the term "intermolecular interaction" refers to an expressed peptide or polypeptide of a virus of the present invention which has the capacity to bind to a target of interest. In one embodiment, the interaction is of high affinity, while in another embodiment, it is of low affinity. In one embodiment, the interaction is mediated by a covalent bond, an ionic bond, a hydrogen bond, Van der Waal's force (a.k.a. weak London dispersion forces), dipole-dipole forces, metallic bonding or any attractive force which provides a physical proximity of between, in one embodiment, 1-5, in another embodiment, 1-20 angstroms.

In another embodiment, the peptide may perform a particular function with a target of interest. In one embodiment, the intermolecular interaction may give rise to a biological, chemical, or physiological consequence. In one embodiment, the consequence may be reversible, while in another embodiment, it may be irreversible. In one embodiment, the intermolecular interaction induces a conformational change, a transformation into a different chemical state of the functional domain or of molecules acted upon by the functional domain, the transduction of an intracellular or intercellular signal, the regulation of gene or protein expression, the regulation of cell growth or death, the activation or inhibition of an immune response, or any combination thereof.

In one embodiment, the term "intermolecular interaction" refers to an affinity between a peptide and a target of interest, i.e. the tendency of a peptide to attach to a specific protein target. The affinity binding is a measure of the intrinsic binding strength of the ligand binding reaction. The intrinsic attractiveness of the binder for the ligand is typically expressed as the equilibrium association constant (Ka) of the reaction. The equilibrium constant Ka=[Ligand−Binder]/[Ligand][Binder], where [ ] represents the molar concentration of the material at equilibrium. The Ka describing the affinity between the peptide and the target of interest can be $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$ M or lower.

In one embodiment, the intermolecular interaction may be between a receptor and a ligand, a receptor and a downstream signal transduction molecule, a receptor and a hormone, a DNA binding protein and a DNA oligonucleotide, an RNA binding protein and an RNA oligonucleotide, an enzyme and a substrate, a toxin and a receptor, a protease and a cleavage site oligonucleotide, an antigen and an antibody, two cell adhesion molecules, or two cytoskeletal proteins. In another embodiment, the intermolecular interaction may refer to an association of any of the above proteins with a protein that enhances binding or activity of the protein or with a protein that inhibits bind binding or activity of the protein. In another embodiment, the intermolecular interaction may involve proteins involved in the regulation of cellular events such as signal transduction, the cell cycle, protein trafficking, targeted proteolysis, cytoskeletal organization and gene expression.

In one embodiment, the environmental conditions such as salt concentration, pH, hydrophobicity, temperature and pressure may affect the nature of an intermolecular interaction, and those factors can be adjusted to the interaction of interest by a person skilled in the art.

Modified Cleavage Site

In one embodiment, the viruses of the present invention further comprise modified cleavage sites. In one embodiment, the term "modified cleavage site" refers to a cleavage site that has a reduced binding affinity to a compound mediating its cleavage. In one embodiment, a reduced binding affinity is a relative determination where binding affinity of the modified cleavage site is lower than that of the natural cleavage site. In one embodiment, the capacity of the modified cleavage site to be cleaved is similar to that of the natural cleavage site. Cleavage may be mediated by proteases or other compounds as will be described hereinbelow.

In one embodiment, the term "reduced binding affinity," "significantly reduced binding affinity" or "reduced affinity", means that the binding affinity of the compound mediating cleavage to the cleavage site is as low as possible using the methods existing in the art, such as ELISA, Gel Shift, Plasmon Resonance (BioCore) etc. In one embodiment, the reduced binding affinity is reflected by changes in off-rate, on-rate, free energy, interatomic distances, binding entropy or binding enthalpy.

In one embodiment, the modified cleavage site of the present invention is proximal to the peptide and protein segment portions of the invention. "Proximal" refers, in one embodiment, to a distance of between 1 and 1000 nucleotides between the modified cleavage site and a peptide or between the modified cleavage site and a protein involved in attachment or infection. In one embodiment, the modified cleavage site and a peptide are inserted in any order between the domain of a protein involved in attachment or infection that anchors the protein to the phage coat and the domain of said protein that mediates attachment. In another embodiment, the modified cleavage site and a peptide are inserted in any order between a domain of a protein that mediates attachment and a domain that mediates infection.

In one embodiment, the present invention also provides an oligonucleotide vector of a recombinant virus of the present invention as described hereinabove. In another embodiment, the present invention provides the use of an oligonucleotide vector of the present invention to prepare a recombinant virus.

In one embodiment, a recombinant virus is created by constructing a recombinant vector using standard recombinant techniques (see, for example, Maniatis, et al., Molecular Cloning, A laboratory Manual (Cold Spring Harbor, 1990) and Ausubel, et al., 1994, Current Protocols In Molecular Biology (John Wiley & Sons, 1996), both incorporated herein by reference) as is well know by one of skill in the art. In one embodiment, cells may be transfected with the vector, allowed to multiply, and DNA isolated therefrom. In another embodiment, viruses may be transduced with the vector.

In one embodiment, a recombinant virus of the present invention may be used in a method to identify a peptide or polypeptide that has an intermolecular interaction with a target of interest as described hereinbelow. In another embodiment, the recombinant virus may be used as part of a kit for identifying a peptide or polypeptide that has an intermolecular interaction with a target of interest, as described hereinbelow. In another embodiment, the recombinant virus may be used in a method to identify an agonistic feature, an antagonistic feature of a peptide or polypeptide that has an intermolecular interaction with a receptor of interest, as described hereinbelow. In another embodiment, the recombinant virus may be used in a method to identify a peptide or polypeptide that inhibits an enzyme of interest, as described hereinbelow. In another embodiment, the recombinant virus may be used in a method to identify a peptide or polypeptide that has a functional feature with a receptor of interest, as described hereinbelow.

Recombinant Virus Library

In one embodiment, a recombinant virus library of the present invention comprises a plurality of viruses as described hereinabove. In one embodiment, each virus of the virus library comprises a peptide that differs by at least one amino acid from a peptide expressed by another virus of the virus library. In one embodiment, the viruses of the present invention comprise peptides involved in an intermolecular interaction. The peptides can be in one embodiment, conveniently selected from any peptide library. In one embodiment, they are selected from random peptide libraries, in another embodiment, combinatorial peptide libraries, while in another embodiment, simulated molecular evolution peptide libraries.

In one embodiment, a random peptide library may generate a collection of peptides in which the probability of finding a particular amino acid at a given position of the peptide is the same for all amino acids. In another embodiment, a bias is introduced into the library. For example, a bias that a lysine occurs every fifth amino acid or that positions 4, 8, and 9 of a decapeptide library be fixed to include only arginine may be specified. Clearly, many types of biases can be contemplated, and this invention is not restricted to any particular bias.

In another embodiment, the peptide or polypeptide library is created as is well known in the art. For example, in one embodiment, a sample of genomic DNA is mechanically sheared or partly digested by restriction enzymes to form large fragments. In one embodiment, this population of overlapping DNA fragments may then be separated by gel electrophoresis to isolate a set of a particular length (15 kb for example). In one embodiment, synthetic linkers may be attached to the ends of these fragments, in one embodiment, cohesive ends may be formed, while in another embodiment, blunt ends may be formed.

In one embodiment, the fragments are then inserted into a vector. In one embodiment, the recombinant vector represents the virus of this invention. In one embodiment, the vector is a plasmid, a bacmid, a phagemid, a cosmid, a phage, a virus or an artificial chromosome. In one embodiment, the vector is derived from a bacteriophage, which infects *E. coli*. In one embodiment, the vector is derived from a lambda phage, M13, fd, f1, or T4. Cells may be transfected with the vector, and DNA isolated therefrom. In one embodiment, cells are propagated so the library can be used repeatedly.

As described above, the virus library may utilize, in one embodiment, a recombinant plasmids or cosmids. In one embodiment, the term "plasmid" is meant to refer to an autonomously replicating extrachromosomal DNA molecule or other genetic particle, often, but not always, comprised of circular double-stranded DNA. Plasmids may become incorporated into the genome of the host or may remain independent. In one embodiment, the term "cosmid" is meant to refer to a hybrid plasmid that contains cos sites at each end. Cos sites are recognized during head filling of lambda phages. Cosmids are useful for cloning large segments of foreign DNA (up to 50 kb).

In another embodiment, the library comprises a plurality of polypeptides from a polypeptide expression library. The polypeptide expression library may be obtained, in one embodiment, from cDNA, fragmented genomic DNA, etc. In one embodiment, the library is a cDNA library comprising total poly A+ RNA of a given organism. In one embodiment, the polypeptide is labeled using a label as described hereinbelow.

In one embodiment, the recombinant virus library may be used in a method to identify a peptide or polypeptide that has an intermolecular interaction with a target of interest as described hereinbelow. In another embodiment, the library may be used as part of a kit for identifying a peptide or polypeptide that has an intermolecular interaction with a target of interest, as described hereinbelow. In another embodiment, the library may be used in a method to identify an agonistic feature, an antagonistic feature of a peptide or polypeptide that has an intermolecular interaction with a receptor of interest, as described hereinbelow. In another embodiment, the library may be used in a method to identify a peptide or polypeptide that inhibits an enzyme of interest, as described hereinbelow.

Host Cells

In one embodiment, the invention comprises a cell comprising a recombinant virus of the present invention as described hereinabove. In another embodiment, the invention comprises a plurality of cells comprising a recombinant virus library of the present invention as described hereinabove. "A plurality of cells" is meant to indicate more than one cell. Cell types may include but are not limited to mammalian, insect, plant, or bacterial cells.

In one embodiment, the terms "cell," "cell line," and "cell culture" may be used interchangeably. In one embodiment, all of these terms also include their progeny, which is any and all subsequent generations. It is understood that all progeny may not be identical due to deliberate or inadvertent mutations. In one embodiment, host cells will have been engineered to express a screenable or selectable marker which is activated by the transcription factor that is part of a fusion protein.

In the context of expressing a heterologous nucleic acid sequence, "host cell" refers to a prokaryotic or eukaryotic cell that is capable of replicating a vector and/or expressing a heterologous gene encoded by a vector. When host cells are "transfected", "transformed", or "transduced" with nucleic acid molecules, they are referred to as "engineered" or "recombinant" cells or host cells, e.g., a cell into which an non-endogenous nucleic acid sequence, such as, for example, a vector, has been introduced. Therefore, recombinant cells are distinguishable from naturally-occurring cells which do not contain a recombinantly introduced nucleic acid. In one embodiment, "non-endogenous" refer to a molecule that it is foreign to the cell into which it is being introduced. In one embodiment, the non-endogenous molecule is DNA. In another embodiment, non-endogenous refers to a nucleic acid sequence that is homologous to a sequence in the cell but is in a position within the host cell nucleic acid in which the sequence is ordinarily not found.

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F−, lambda−, prototrophic, ATCC No. 273325), DH5α, JM109, and KC8, bacilli such as *Bacillus subtilis*, and other enterobacteriaceae such as *Salmonella typhimurium*, *Serratia marcescens*, various *Pseudomonas* species, as well as a number of commercially available bacterial hosts such as SURER Competent Cells and SOLOPACK™ Gold Cells (STRATAGENE, La Jolla). In certain embodiments, bacterial cells such as *E. coli* LE392 are particularly contemplated as host cells for phage viruses. In one embodiment, *E. Coli* may be used as a host cell. Useful strain of *E. Coli* may be determined using Genbank (http://www.ncbi.nlm.nih.gov/Genbank/index.html) by one skilled in the art.

Examples of eukaryotic host cells for replication and/or expression of a vector include, but are not limited to, HeLa, NIH3T3, Jurkat, 293, COS, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

In another embodiment, the present invention also provides a plurality of oligonucleotide vectors of the recombinant virus library of the present invention as described hereinabove. In another embodiment, the present invention provides the use of oligonucleotide vectors of the present invention to prepare a recombinant virus library.

In one embodiment, a recombinant virus library of the present invention may be used in a method to identify a peptide or polypeptide that has an intermolecular interaction with a target of interest as described hereinbelow. In another embodiment, the recombinant virus library may be used as part of a kit for identifying a peptide or polypeptide that has an intermolecular interaction with a target of interest, as described hereinbelow. In another embodiment, the recombinant virus library may be used in a method to identify an agonistic feature, an antagonistic feature of a peptide or polypeptide that has an intermolecular interaction with a receptor of interest, as described hereinbelow. In another embodiment, the recombinant virus library may be used in a method to identify a peptide or polypeptide that inhibits an enzyme of interest, as described hereinbelow. In another embodiment, the recombinant virus library may be used in a method to identify a peptide or polypeptide that has a functional feature with a receptor of interest, as described hereinbelow.

Target of Interest Complex

In another embodiment, the invention provides a protein-protein or protein-non-protein complex (referred to herein as "Target of interest (TOI) complex") comprising a protease or functional domain thereof, a target of interest involved in an intermolecular interaction, and a flexible linker that attaches the protease and target of interest.

Protease

In one embodiment, the cleavage site is modified such that a compound mediating cleavage has a reduced binding affinity for said site, as compared to a non-modified cleavage site. In one embodiment, a compound that cleaves DNA is a protease or other enzyme. "Protease" refers to the enzymes included under E.C.3.4. (Cf. Kirk-Othmer, Encyclopedia of Chemical Technology, 3rd edition, volume 9, pages 173-223, J. Wiley 1980; E. Pfleiderer and R. Reiner in H. J. Rehm & G. Reed, Biotechnology, volume 6b, pages 729-742, VCH 1988; K. Aunstrup in Industrial Aspects of Biochemistry, B. Spencer, editor, volume 30(I), pages 23-46, North Holland 1974). Proteases are well characterized enzymes that cleave other proteins at a particular site. One family, the Ser/Thr proteases, cleave at serine and threonine residues. Other proteases include cysteine or thiol proteases, aspartic proteases, metalloproteinases, aminopeptidases, di & tripeptidases, carboxypeptidases, and peptidyl peptidases. The choice of these is left to the skilled artisan and certainly need not be limited to the molecules described herein. It is well known that enzymes have catalytic domains and these can be used in place of full length proteases. Such are encompassed by the invention as well. One preferred embodiment is the ubiquitin binding protein-1 protease, or an active portion thereof. Other specific cleavage sites for proteases may also be used, as will be clear to the skilled artisan.

The proteases of the invention may be, for example, specific ubiquitin protease UBP1, aspartyl protease, herpes protease, herpes simplex 1 protease, retroviral protease, cysteine protease, matrix metalloproteinase, interstitial collagenase (MMP-1), gelatinase A (MMP-2) and gelatinase B (MMP-9); serine proteases such as plasminogen activator (PA) and the like. However, the methods of the present invention are not limited to these particular proteases. Endogenous proteolytic enzymes provide a variety of useful functions, including the degradation of invading organisms, antigen-antibody complexes, and certain tissue proteins that are no longer necessary. The serine proteases comprise a large family of enzymes that use an activated serine residue in the substrate-binding site to catalytically hydrolyze peptide bonds the aspartate-specific cysteine proteases (AS-CPs).

In one embodiment, any member of a particular family of proteases may be used in place of the protease specifically described. Further, any member of a particular family of proteases may be used on a particular modified cleavage site.

In one embodiment, there is provided a recombinant virus library in which at least one virus comprises a peptide and a modified cleavage site located proximally to a protein or protein fragment, comprising segments which are involved in viral attachment, infection, or a combination thereof and a protein or protein fragment, comprising segments that serve as an anchor. In another embodiment, there is provided a recombinant virus library in which at least one virus comprises a peptide and a modified cleavage site located between a protein or protein fragment, comprising segments which are involved in viral attachment, infection, or a combination thereof and a protein or protein fragment, comprising segments that serve as an anchor. An "anchoring protein or fragment" refers to a protein or fragment that connects another protein or fragment to a larger body such as a cell wall or cell membrane.

Linkers

In one embodiment, all components of the TOI complex are separated by long flexible linkers or spacers to enable a good degree of freedom that would allow the components of the system to interact with each other. In one embodiment, the linkers allow structural folding, while in another embodiment, they allow hydrogen bonding.

The linkers can be, without limitation, leucine zipper, SH2 domains, PDZ domains, antibody domains, and the like. Any other flexible linker could be used as well. In one embodiment, the flexible linker is at least 3 amino acids in length. In another embodiment the flexible linker is at least 5 amino acids in length. In another embodiment the flexible linker is at least 7 amino acids in length. In another embodiment the flexible linker is at least 9 amino acids in length. In another embodiment the flexible linker is at least 13 amino acids in length. In another embodiment the flexible linker is at least 15 amino acids in length. In another embodiment the flexible linker is at least 18 amino acids in length. In another embodiment the flexible linker is between 1 and 20 amino acids in length. In another embodiment the flexible linker is between 3 and 15 amino acids in length. In another embodiment the flexible linker is between 3 and 10 amino acids in length. In another embodiment the flexible linker is between 5 and 10 amino acids in length. In another embodiment the flexible linker is between 10 and 15 amino acids in length. In another embodiment the flexible linker is between 15 and 20 amino acids in length. In another embodiment, the target of interest is bound directly to a protease without a linker.

Target of Interest

In one embodiment, the TOI complex of the present invention comprises a target of interest. The target of interest is in one embodiment, a receptor. In one embodiment, the term "receptor" refers to receptors that bind peptide messengers with high affinity and regulate intracellular signals which influence the behavior of cells. In another embodiment, the target of interest is an agonist. In another embodiment, the target of interest is an antagonist. In another embodiment, the target of interest is an antibody. In another embodiment, the target of interest is an antigen. In another embodiment, the target of interest is an enzyme. In another embodiment, the target of interest is an enzyme-activating substrate. In another embodiment, the target of interest is an inhibitor. In another embodiment, the target of interest is a hormone. In another embodiment, the target of interest is a cytoskeletal protein. In another embodiment, the target of interest is a toxin. In another embodiment, the target of interest is synthetic or physiological polymer. In another embodiment, the target of interest is a small organic molecule. In another embodiment, the target of interest is a DNA sequence. In another embodiment, the target of interest is a RNA sequence. In another embodiment, the target of interest is an oligonucleotide. In another embodiment, the target of interest is a transcriptional activator or repressor. In another embodiment, the target of interest is a translational activator or repressor. In another embodiment, the target of interest is a functional fragment of an agonist, antagonist, receptor, antibody, antigen, enzyme, enzyme activator, enzyme inhibitor, enzyme substrate, hormone, regulatory protein, cytoskeletal protein, toxin, synthetic or physiological polymer, small organic molecule, DNA, RNA, oligonucleotide, transcriptional activator or repressor, translational activator or repressor.

In another embodiment, the target of interest is a carrier. In another embodiment, the target of interest is an information protein. Information proteins are proteins involved in DNA replication, repair, recombination and transcription. In another embodiment, the target of interest is a structural protein. Structural proteins are fibrous proteins, including keratins, actin, myosin, and collagens involved building components inside the cell and around it. In another embodiment, the target of interest is a regulatory protein. Regulatory proteins command the numerous interactions that govern the expression and replication of genes, the performance of enzymes, the interplay between cells and their environment, and many other manifestations. In another embodiment, the target of interest is a DNA or RNA binding peptide.

In one embodiment, the target materials may be organic macromolecules, such as polypeptides, lipids, polynucleic acids, and polysaccharides, but are not so limited. Almost any molecule that is stable in aqueous solvent may be used as a target. The following list of possible targets is given as illustration and not as limitation. The categories are not strictly mutually exclusive. The omission of any category is not to be construed to imply that said category is unsuitable as a target. Merck Index refers to the Eleventh Edition.

In one embodiment, the target of interest may be a peptide such as human β endorphin (Merck Index 3528), dynorphin (MI 3458), Substance P (MI 8834), Porcine somatostatin (MI 8671), human atrial natriuretic factor (MI 887), human calcitonin, or glucagons. In another embodiment, the target of interest may be a hormone such as human TNF (MI-9411), Interleukin-1 (MI 4895), Interferon-.lambda. (MI 4894), Thyrotropin (MI 9709), Interferon-α (MI 4892), or Insulin (MI 4887, p. 789). In another embodiment, the target of interest may be an enzyme such as human neutrophil elastase, Human thrombin, human Cathepsin G, human tryptase, human chymase, human blood clotting Factor Xa, any retro-viral Poi protease, any retro-viral Gag protease, dihydrofolate reductase, *Pseudomonas putida* cytochrome $P450_{CAM}$, human pyruvate kinase, *E. Coli* pyruvate kinase, jack bean urease, or aspartate transcarbamylase (*E. coli*), ras protein, or any protein-tyrosine kinase. In another embodiment, the target of interest may be an inhibitor such as aprotinin (MI 784), human el-anti-trypsin, or phage .lambda. cI (inhibits DNA transcription). In another embodiment, the target of interest may be a receptor, such as TNF receptor, IgE receptor, LamB, CD4, or IL-1 receptor. In another embodiment, the target of interest may be a toxin such as ricin (also an enzyme), a Conotoxin GI, mellitin, *Bordetella pertussis* adenylate cyclase (also an enzyme), or *Pseudomonas aeruginosa* hemolysin. In another embodiment, the target of interest may be another protein such as horse heart myoglobin, human sickle-cell haemoglobin, human deoxy haemoglobin, human CO haemoglobin, human low-density lipoprotein (a lipoprotein), human IgG (combining site removed or blocked) (a glycoprotein), influenza haemagglutinin, phage .lambda. capsid, fibrinogen, HIV-1 gp120, *Neisseria gonorrhoeae* pilin, fibril or flagellar protein from spirochaete bacterial species such as those that cause syphilis, Lyme disease, or relapsing fever, or pro-enzymes such as prothrombin or trypsinogen. In another embodiment, the target of interest may be an insoluble protein such as silk, human elastin, keratin, collagen, or fibrin. In another embodiment, the target of interest may be a nucleic acid such as DNA, RNA, yeast Phe tRNA, ribosomal RNA, or a segment of mRNA. In another embodiment, the target of interest may be an organic monomer (not peptide, protein, or nucleic acid) such as cholesterol, aspartame, bilirubin, morphine, codeine, heroine, dichlorodiphenyltrichlorethane (DDT), prostaglandin PGE2, actinomycin, 2,2,3 trimethyl-decane, Buckminsterfullerene, or cortavazol (MI 2536, p. 397). In another embodiment, the target of interest may be an organic polymer such as cellulose or chitin. In another embodiment, the target of interest may be O-antigen of *Salmonella enteritidis* (a lipopolysaccharide). In another embodiment, the target of interest may be an inorganic compound such as asbestos, zeolites, hydroxylapatite, 111 face of crystalline silicon, paulingite, U (IV) (uranium ions), or Au(III) (gold ions). In another embodiment, the target of interest may be an organometallic compound such as iron (III) haem, cobalt haem, cobalamine, or (isopropylamino)$_6$ Cr(III).

In one embodiment, the peptide or polypeptide may represent a cognate peptide of any of the peptides or polypeptides described herein. In another embodiment, said target of interest has one or more intermolecular interactions with a cognate ligand, antigen, enzyme substrate, enzyme, regulatory protein, or cytoskeletal protein expressed on the surface of a recombinant virus. An "enzyme substrate" is a substrate on which an enzyme acts to catalyze a reaction. In another embodiment, said target of interest has one or more intermolecular interactions with an agonist, antagonist, antigen, enzyme activator, enzyme inhibitor, hormone, regulatory protein, toxin, or a functional fragment thereof.

In one embodiment, the target of interest is a peptide, which has approximately 6 to 60 amino acid residues. In another embodiment, a peptide target of interest has approximately 20-100 amino acids, or in another embodiment 20-50 amino acids. In the case of a bile acid receptor, for example, the target of interest may be a bile acid, such as cholic acid or cholesterol, and may have a molecular weight of about 300 to about 600 kDa. If the functional domain relates to transcriptional control, the target of interest may be a portion of a transcriptional factor, which may bind to a region of a gene of interest or to an RNA polymerase. The target of interest may even be a nucleoside analog, such as cordycepin or the triphosphate thereof, capable of inhibiting RNA biosynthesis. The target of interest may also be the carbohydrate portion of a glycoprotein, which may have a selective affinity for the asialoglycoprotein receptor, or the repeating glucan unit that exhibits a selective affinity for cellulose binding domain or the active site of heparinase.

In one embodiment, the target of interest may refer to a functional domain of a target of interest. In another embodiment, the functional domain may include a ligand binding domain, an activation domain, or any other domain of a target of interest.

In one embodiment, the target of interest is labeled. In another embodiment, the TOT complex additionally comprises a tag that allows affinity purification. In another embodiment, the tag is a His-Tag.

As described hereinabove, vectors include plasmids, cosmids, viruses (bacteriophage, mammalian viruses, and plant viruses), and artificial chromosomes (e.g., YACs). One of skill in the art would be well equipped to construct a vector through standard recombinant techniques (see, for example, Maniatis, et al., Molecular Cloning, A laboratory Manual (Cold Spring Harbor, 1990) and Ausubel, et al., 1994, Current Protocols In Molecular Biology (John Wiley & Sons, 1996), both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences" which refer to nucleic acid sequences necessary for the transcription and possibly translation of an operably linked coding sequence in a particular host cell. In addition to control sequences that govern transcription and translation, vectors and expression vectors may contain nucleotide sequences that serve other functions as well and are described infra.

In one embodiment, the TOI complex of the present invention is produced by methods known in the art. In one embodiment, the TOI complex is produced by in vitro translation. In certain embodiments, a plasmid vector is contemplated for use in cloning and gene transfer. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides an easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally between 2 and 24 h, the cells are collected by centrifugation and washed to remove residual media.

In another embodiment, prokaryotic vectors can be used to transform eukaryotic host cells. However, it may be desirable to select vectors that have been modified for the specific purpose of expressing proteins in eukaryotic host cells. Expression systems have been designed for regulated and/or high level expression in such cells. For example, the insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM from CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

The construct may contain additional 5' and/or 3' elements, such as promoters, enhancers, poly A sequences, and so forth. The elements may be derived from the host cell, i.e., homologous to the host, or they may be derived from distinct source, i.e., heterologous. It is to be understood that various elements of the vector may be manipulated such as, for example, promoters, enhancers, high copy or low copy, etc as will be understood by one skilled in the art. Any manipulation of the vector is considered to be part of the present invention.

Vectors can include a multiple cloning site (MCS), donor and/or acceptor splicing sites, termination signals, polyadenylation sites, etc., as are well known to those of skill in the art of recombinant technology.

In order to propagate a vector in a host cell, it may contain one or more origins of replication (often termed "ori") sites', which are specific nucleotide sequences at which replication is initiated. Alternatively, an autonomously replicating sequence (ARS) can be employed if the host cell is yeast.

Transformation Methodology

Suitable methods for nucleic acid delivery for use with the current invention are believed to include virtually any method by which a nucleic acid molecule (e.g., DNA) can be introduced into a cell as described herein or as would be known to one of ordinary skill in the art. Such methods include, but are not limited to, direct delivery of DNA such as by ex vivo transfection, including microinjection; by electroporation; by calcium phosphate precipitation; by using DEAE-dextran followed by polyethylene glycol; by direct sonic loading; by liposome mediated transfection and receptor-mediated transfection; by PEG-mediated transformation of protoplasts; by desiccation/inhibition-mediated DNA uptake, and any combination of such methods, as are well known to those skilled in the art.

In one embodiment, TOI complexes comprising non-protein components, once created by any method known in the art, are tested for binding specificity using any of the methods known in the art including but not limited to electrophoretic mobility shift assay (EMSA, Gel Shift Assay, or Band Shift Assay), footprinting, and methylation interference with a known ligand of the target of interest as a probe. In another embodiment, TOI complexes comprising protein components, once created by any method known in the art, are tested for binding specificity using any of the methods known in the art including but not limited to co-immunoprecipitation, yeast two-hybrid, density gradient centrifugation, GFP tagging (fluorescence resonance energy transfer (FRET)), protein affinity chromatography, protein arrays, surface plasmon resonance (SPR) and GST pulldown assay with a known ligand of the target of interest as a probe. These same methods will be used to confirm the interaction of the target of interest and a peptide expressed by a recombinant virus.

In another embodiment, the present invention provides the use of any of the peptides, polypeptides, proteins, protein fragments, and TOI complexes of the present invention in executing the methods of this invention. In another embodiment, the TOI complexes are In one embodiment, a TOI complex of the present invention may be used in a method to identify a peptide or polypeptide that has an intermolecular interaction with a target of interest as described hereinbelow. In another embodiment, the TOI complex may be used as part of a kit for identifying a peptide or polypeptide that has an intermolecular interaction with a target of interest, as described hereinbelow. In another embodiment, the TOI complex may be used in a method to identify an agonistic feature, an antagonistic feature of a peptide or polypeptide that has an intermolecular interaction with a receptor of interest, as described hereinbelow. In another embodiment, the TOI complex may be used in a method to identify a peptide or polypeptide that inhibits an enzyme of interest, as described hereinbelow. In another embodiment, the TOI complex may be used in a method to identify a peptide or polypeptide that has a functional feature with a receptor of interest, as described hereinbelow.

Method of Identifying a Peptide with an Intermolecular Interaction

In another embodiment, this invention provides a method of identifying a peptide or polypeptide having an intermolecular interaction with a target of interest by employing a recombinant virus or recombinant virus library of the present invention with a TOI complex also of the present invention or any embodiment thereof. The method comprises the steps of: contacting a recombinant virus library as exemplified hereinabove with a TOI complex as exemplified hereinabove, contacting said library with a plurality of cells, isolating viruses that did not infect said cells, providing infectious clones of isolated viruses by amplifying and expressing the genomes of said isolated viruses, repeating the above steps, and identifying peptides expressed by said viruses whereby intermolecular interactions between said target of interest and a peptide expressed by said recombinant virus result in said protease being in close proximity to said cleavage site, resulting in cleavage of said protein or protein fragment, comprising segments which are involved in viral attachment to, infection of, or a combination thereof of cells, and prevention of entry of a virus comprising a peptide involved in intermolecular interactions into said cells.

Figure 2:
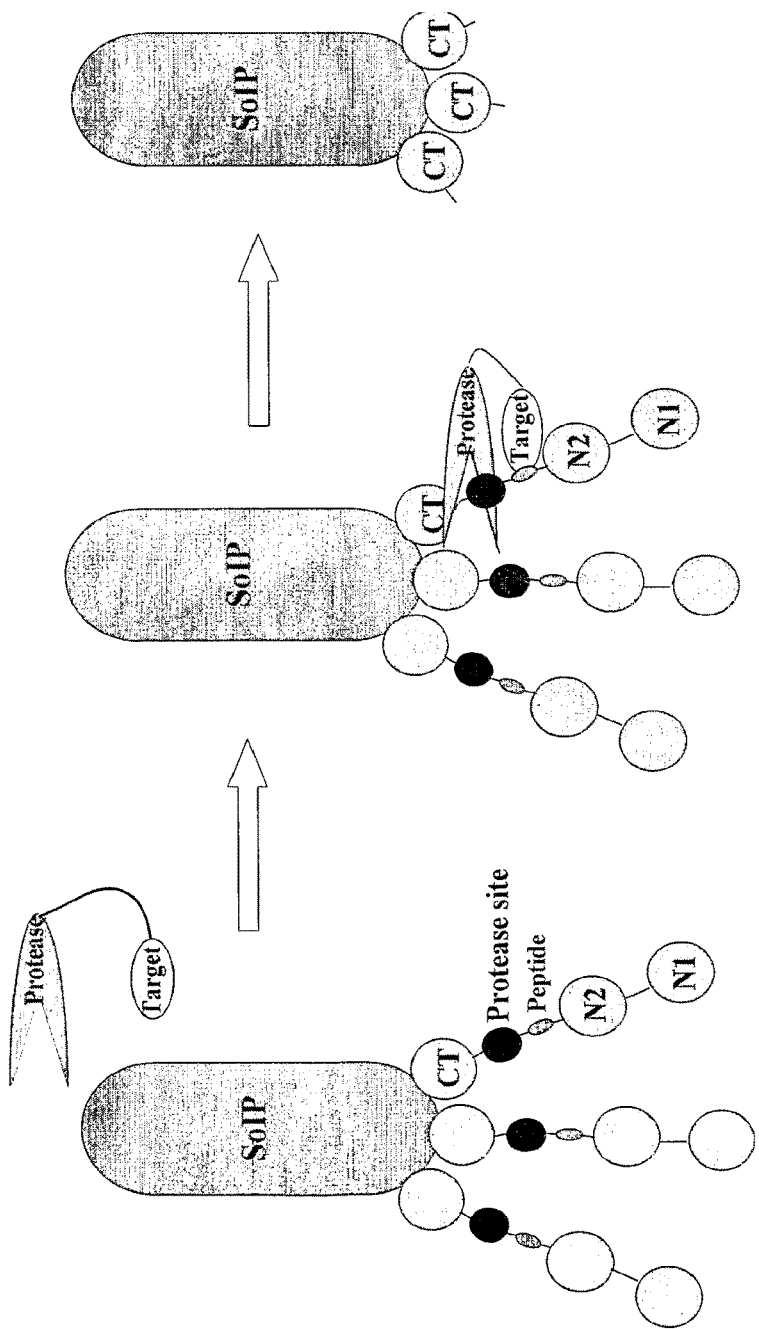
FIG. 2 is an illustration in one embodiment of a genetically engineered infective M13 bacteriophage termed SoIP. SoIP comprises the pIII domains of wild type bacteriophage, but with an insertion of a modified protease site and a peptide between the N2 and CT domains of each pIII protein. Cleavage of the N1 and N2 domains of pIII occurs in SoIP when a target protein (Target) which is fused to a protease (Protease) binds to the peptide expressed on the pIII protein (Peptide). The resultant proximity of Protease to the modified protease site results in proteolysis of N1, N2, the peptide, and the modified protease site from the CT domain of pIII and the capsid.

In one embodiment, the method is predicated on the fact that viruses are inhibited or prevented from entry into a host cell as a result of the cleavage of their pIII protein as depicted in FIGS. 1 and 4. In one embodiment, if a protease were to cleave the pIII proteins of a bacteriophage at a site between the N2 and CT domains of pIII, the M13 bacteriophage would not be infective. In another embodiment, if a protease were to cleave the pIII proteins of a bacteriophage at a site between the N1 and N2 domains of pIII, the M13 bacteriophage would not be infective. In one embodiment, the pIII protein cleavage is mediated by a protease that was brought into proximity of its cleavage site by the interaction of a target of interest proximal to the protease with a peptide proximal to the modified cleavage site on the pIII protein of the virus as depicted in FIG. 2.

The steps are repeated for any number of cycles deemed sufficient to enrich the fraction for recombinant viruses that harbor peptides that bind to a target of interest and until there is a negligible number of background clones. In one embodiment, background clones refers to clones which harbor peptides that do not bind to a target of interest. In one embodiment, the number of cycles ranges between 3 and 50.

In one embodiment, the identified peptide that has an intermolecular interaction with the target of interest is isolated. In one embodiment, the isolated viruses which have been prevented from entering into cells are found in the medium. The step of the isolation can be performed using methods that are well known in the art. In one embodiment the separation is performed by filtration. In another embodiment the separation is performed by spinning down, for example in a centrifuge. In another embodiment, the separation can be conducted by selectively providing conditions for the maintenance of the infected cells or, alternatively, conditions for the maintenance of the non-infective viruses.

In another embodiment, the isolated viruses which have not infected cells are attached to the surface of the cells, but have not entered said cells. In one embodiment, the present invention further provides a recombinant virus, including a bacteriophage, comprising a label such that the label can be directly detected. The recombinant virus can express on its surface a peptide that has an intermolecular interaction with a selected protein. By "directly detected" is meant that the recombinant virus be labeled in advance and still comprise a peptide that binds its target upon addition of the target. Furthermore, by "label" is meant a means for visualization, such as a recognition site for direct phosphorylation, biotinylation, chemical linkages, etc. engineered into the recombinant virus, or such as a directly visualized label requiring no chemical reaction to detect, e.g., the recombinant virus expresses a fluorescent protein or is labeled by a radioactive moiety. Recombinant virus can be modified to include a label in advance, allowed to interact with the fusion protein of the present invention, be exposed to cells, and the cells separated from free recombinant virus in solution. Recombinant virus can then be visualized to detect the presence and localization of the recombinant virus, whether in the solution or in the cell fraction. Visualization may or may not require a chemical reaction. An example of a fluorescent protein is the green fluorescent protein (GFP) originally isolated from the jellyfish Aequorea Victoria. Another example of a fluorescent protein is the green fluorescent protein originally isolated from *Renilla* reniforms, which demonstrates a single absorption peak at 498 nm and an emission peak at 509 nm. (Cubitt, et el. (1995) TUBS 20: 448-455).

The amino acid sequence of the identified peptide can be determined directly by conventional means of amino acid sequencing, or the coding sequence of the DNA encoding the polypeptide can frequently be determined more conveniently by use of standard DNA sequencing methods. The primary amino acid sequence can then be deduced from the corresponding DNA sequence.

If the amino acid sequence is to be determined from the polypeptide itself, one may use micro sequencing techniques. The sequencing technique may include mass spectroscopy.

The nucleic acid and protein sequences of the present invention can further be used as a "query sequence" to perform a search against sequence databases to, for example, identify other family members or related sequences. Such searches can be performed using the NBLAST and) (BLAST programs (version 2.0) of Altschul, et al. (J. Mol. Biol. 215:403-10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3 to obtain amino acid sequences homologous to the proteins of the invention. To obtain gapped alignments for comparison purposes, Gapped BLAST can be utilized as described in Altschul et al. (Nucleic Acids Res. 25(17): 3389-3402 (1997)). When utilizing BLAST and gapped BLAST programs, the default parameters of the respective programs (e.g., XBLAST and NBLAST) can be used.

In the method of the present invention, the recombinant virus library is contacted with a plurality of cells. The step of "contacting" or "introducing" refers hereinafter to bringing a solution comprising at least one element, (e.g., the recombinant virus) in contact with another element (e.g., the cells or a composition which comprise the cells).

In one embodiment, the recombinant virus library of the method of identifying a peptide or polypeptide with an intermolecular interaction with a target of interest is produced in a phage. In another embodiment, the recombinant library is produced in M13 bacteriophage.

In another embodiment, the recombinant viruses comprise peptides with mutations that abrogate binding to target of interest.

In one embodiment, the term "mutation" refers to an insertion, deletion, or substitution of one or more natural or wild type nucleic acids for alternate nucleic acids. In one embodiment, the term "abrogate" means to abolish, do away with, or annul.

Epitope Mapping

In another embodiment, the peptide identified by this invention can serve for epitope mapping of the target of interest. "Epitope mapping" refers to methods used for studying the interactions of antibodies with specific regions of protein antigens.

In one embodiment, the polypeptide is labeled. In another embodiment, the target of interest is labeled. A wide range of labels can be used, including but not limited to conjugating the target to biotin by conventional means. Alternatively, the label may comprise a fluorogen, an enzyme, an epitope, a chromogen, or a radionuclide. The detection means employed to detect the label will depend on the nature of the label and are known in the art, e.g., film to detect a radionuclide; an enzyme substrate that gives rise to a detectable signal to detect the presence of an enzyme; antibody to detect the presence of an epitope, etc.

Solid Support

In one embodiment, the target is not bound to a solid support and is added to the medium by, for example, contacting the solution of the recombinant virus with a solution that comprises the target of interest. In another embodiment, the target of interest of this invention may be bound to a solid support.

Kit

In another embodiment, this invention provides a kit for identifying a peptide or polypeptide involved in an intermolecular interaction with a target of interest comprising a recombinant virus peptide library of the present invention as exemplified hereinabove, a TOI complex of the present invention as exemplified hereinabove, and cells that are susceptible to viral attachment, infection or a combination thereof. In one embodiment, the kit of the present invention comprises a virus of the present invention, a library of the present invention, a TOI complex of the present invention or any combination thereof.

Any of the compositions described herein may be comprised in a kit. The kits will thus comprise, in suitable container means for the vectors or cells of the present invention, and any additional agents that can be used in accordance with the present invention. In one embodiment, any container of the kit will additionally comprise a preservative, which, in one embodiment, will increase the "shelf life" of the kit component or components to which it is added.

The kits may comprise suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial.

The kits of the present invention also will typically include a means for containing reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The kit optionally further comprises a means for detecting the presence of an interaction between a polypeptide and a target of interest or the absence of an interaction thereof.

In one embodiment, the recombinant virus library of the kit for identifying a peptide or polypeptide with an intermolecular interaction with a target of interest is produced in a phage. In another embodiment, the recombinant library is produced in M13 bacteriophage. In another embodiment, the recombinant viruses of the kit comprise peptides with mutations that abrogate binding to target of interest. In another embodiment, the peptide identified by said kit can be used for epitope mapping of the target of interest. In another embodiment, the target of interest of the kit is not bound to a solid support.

Identifying an Agonist or Antagonist

It should be likewise be apparent that the function of polypeptides can be identified, i.e. this invention enables, in one embodiment, to determine whether the peptide is an agonist or an antagonist to a receptor or if it is an inhibitor of an enzyme. In one embodiment, this invention provides a method of identifying a peptide or polypeptide that has an agonistic or an antagonistic effect on the target of interest of the invention by employing a recombinant virus or recombinant virus library of the present invention with a TOI complex also of the present invention or any embodiment thereof.

It should likewise be apparent that a wide range of peptides or polypeptides that have an agonistic or an antagonistic effect on the target of interest of the invention, can be identified by the process of the invention, which comprises: (a) contacting the recombinant virus library as described hereinabove with a plurality of complexes as described hereinabove wherein the target of interest is a receptor; (b) contacting said recombinant virus library of step (a) with cells; (c) isolating viruses in (b) which have not infected said cells; (d) providing infectious clones of first isolated viruses of (c) by amplifying and expressing the genomes of said first isolated viruses; (e) contacting infectious clones of viruses of step (c) with the receptor of interest, wherein said receptor is not attached to a protease; (f) contacting the viruses of step (e) with a protein attached to a protease via a flexible linker, wherein said protein is involved in the downstream signal transduction pathway of said receptor of interest; (g) contacting the viruses of step (f) with cells; (h) separating viruses in (g) that have not infected said cells from viruses which have infected cells; (i) providing infectious clones of second isolated viruses of step (h) by amplifying and expressing the genomes of said second isolated viruses; (j) repeating steps (a)-(i); and (k) identifying peptides expressed by the viruses in step (h), whereby viruses which have not infected said cells in (h) express a peptide which has agonistic activity for said receptor of interest, and viruses which have infected said cells in (h) express a peptide which has antagonistic activity for said receptor.

Knowing that a polypeptide exhibits a selective affinity to a target of interest, one may attempt to identify a drug that can exert an effect on the polypeptide-target of interest interaction, e.g., either as an agonist or as an antagonist of the interaction. With this assay, one can screen a collection of candidate "drugs" for the one exhibiting the most desired characteristic, e.g., the most efficacious in reverting the required vital process or function and whether it is an agonist or an antagonist to the target of interest.

In one embodiment, the term "agonist" refers to an endogenous substance or drug that can interact with a receptor and initiate a physiological or a pharmacological response characteristic of that receptor (contraction, relaxation, secretion, enzyme activation, etc.)

In one embodiment, the term "antagonist" refers to an endogenous substance or drug that blocks or nullifies an action of another endogenous substance or drug, such as a drug that binds to a receptor without initiating a physiological or a pharmacological response characteristic of that receptor.

In order to isolate a peptide which has an antagonistic feature, the medium further comprises a ligand, which naturally binds the receptor of interest, and other components, may be added if required for the activation of the receptor, for example without limitation calcium, sodium, and magnesium ions, ATP, EDTA, DTT, etc.

In one embodiment, the receptor of interest may be any receptor from the following families, including subtypes thereof: 5-Hydroxytryptamine, Acetylcholine (muscarinic), Adenosine, Adrenoceptors, Anaphylatoxin, Angiotensin, Apelin, Bombesin, Bradykinin, Cannabinoid, Chemokine, Cholecystokinin, Dopamine, Endothelin, Free fatty acid, G protein-coupled bile acid, Galanin, Motilin, Ghrelin, Glycoprotein hormone, GnRH, Histamine, KiSS1-derived peptide, Leukotriene and lipoxin, Lysophospholipid, Melanin-concentrating hormone, Melanocortin, Melatonin, Neuromedin U, Neuropeptide FF/neuropeptide AF, Neuropeptide S, Neuropeptide W/neuropeptide B, Neuropeptide Y, Neurotensin, N-Formylpeptide family, Nicotinic acid, Opioid, Opsin-like, Orexin (hypocretin), P2Y, Peptide P518, Platelet-activating factor, Prokineticin, Prolactin-releasing peptide, Prostanoid, Protease-activated, Relaxin, Somatostatin, SPC/LPC, Tachykinin, Trace Amine, TRH, Urotensin, Vasopressin/oxytocin, OrphanA1, OrphanA2, OrphanA3, OrphanA4, OrphanA6, OrphanA7, OrphanA9, OrphanA12, OrphanA13, OrphanA14, OrphanA15, OrphanLGR, OrphanSREB, Orphan, Orphan (chemokine receptor-like), Orphan (Mas-related), Orphan (melatonin-like), Orphan (P2Y-like), Orphan (trace amine-like), or Other orphan genes. In another embodiment, the receptor of interest may be any receptor from the following families, including subtypes thereof: Calcitonin receptor family, CRF receptor family, CRF receptor family, Glucagon receptor family, PTH receptor family, VIP/PACAP, LNB7TM, LNB7TM:Brain specific angiogenesis inhibitor, LNB7TM:Proto-cadherin, LNB7TM:EGF, mucin-like receptor, LNB7TM, or LNB7TM:Latrophilin substrate. In another embodiment, the receptor of interest may be any receptor from the following families, including subtypes thereof: $GABA_B$, Metabotropic glutamate, Calcium sensor, GPRC5, or Unclassified.

In another embodiment, the receptor of interest may be TNF receptor, IgE receptor, LamB, CD4, or IL-1 receptor, any of the serotonergic receptors, cholinergic receptors, rhodopsin receptor, thyroid-stimulating hormone receptor, follicle-stimulating hormone receptor, any of the odorant receptors, and parathyroid hormone receptor. In another embodiment, the receptor of interest may be a nuclear receptor such as an estrogen receptor, progesterone receptor, androgen receptor, thyroid receptor, Vitamin D receptor, glucocorticoid receptor, mineralocorticoid receptor, peroxisome proliferator-activated receptor, insulin receptor, gonadotrophin-releasing hormone receptor, or cathepsin D receptor.

In another embodiment, the protein involved in the downstream signal transduction pathway of the receptor of interest is a guanine nucleotide binding protein (G protein) or any subunit thereof, a small GTPase, a cyclic nucleotide such as cyclic AMP or cyclic GMP, calcium, phosphoinositide derivatives such as phosphatidylinositol-triphosphate ($PIP_3$), Diacylglycerol (DAG) or inositol-triphosphate ($IP_3$), or various protein kinases or phosphatases. In another embodiment, the protein involved in the downstream signal transduction pathway of the receptor of interest is nitric oxide, carbon oxide, ceramide, or lysophosphatic acid.

Identifying an Enzyme Inhibitor

In another embodiment, this invention provides a method for identifying a peptide or polypeptide that inhibits an enzyme of interest by employing a recombinant virus or recombinant virus library of the present invention with a TOI complex also of the present invention or any embodiment thereof. In another embodiment, this invention provides a method for identifying a peptide or polypeptide that inhibits an enzyme of interest comprising the steps of: (a) contacting the recombinant virus library as described hereinabove with a plurality of complexes as described hereinabove wherein the target of interest is an enzyme; (b) contacting said recombinant virus library of step (a) with cells; (c) isolating viruses in (b) which have not infected said cells; (d) providing infectious clones of first isolated viruses of (c) by amplifying and expressing the genomes of said first isolated viruses; (e) contacting infectious clones of viruses of step (c) with the enzyme of interest, wherein said enzyme is not attached to a protease; (f) contacting the viruses of step (e) with a substrate of the enzyme attached to a protease via a flexible linker; (g) contacting the viruses of step (f) with cells; (h) separating viruses in (g) which have not infected said cells from viruses which have infected cells; (i) providing infectious clones of second isolated viruses of step (i) by amplifying and expressing the genomes of said second isolated viruses; (j) repeating steps (a)-(i); and (k) identifying peptides expressed by the viruses in step (h), whereby viruses which have not infected said cells in (h) express a peptide which does not affect said enzyme of interest, and viruses which have infected said cells in (h) express a peptide which inhibits said enzyme.

Identifying a Peptide with a Functional Feature

In another embodiment, this invention provides a method of identifying a peptide or polypeptide which has a functional feature with a receptor of interest by employing a recombinant virus or recombinant virus library of the present invention with a TOI complex also of the present invention or any embodiment thereof. In another embodiment, this invention provides a method of identifying a peptide or polypeptide which has a functional feature with a receptor of interest comprising the steps of: (a) contacting the recombinant virus library as described hereinabove with a plurality of complexes as described hereinabove wherein the target of interest is a receptor; (b) contacting said recombinant virus library of step (a) with cells; (c) isolating viruses in (b) which have not infected said cells; (d) providing infectious clones of first isolated viruses of (c) by amplifying and expressing the genomes of said first isolated viruses; (e) contacting infectious clones of viruses of step (c) with the receptor of interest, wherein said receptor is not attached to a protease; (f) contacting the viruses of step (e) with a ligand of the receptor attached to a protease via a flexible linker; (g) contacting the viruses of step (f) with cells; (h) separating viruses in (g) which have not infected said cells from viruses which have infected cells; (i) providing infectious clones of second isolated viruses of step (i) by amplifying and expressing the genomes of said second isolated viruses; (j) repeating steps (a)-(i); and (k) identifying peptides expressed by the viruses in step (h), whereby viruses which have not infected said cells in (h) express a peptide which does not have a functional feature, and viruses which have infected said cells in (h) express a peptide which has a functional feature with regards to said receptor of interest.

In one embodiment, the recombinant virus library of the method for identifying a peptide or polypeptide with an agonistic, antagonistic, enzyme inhibitory, or functional effect with respect to a target of interest is produced in a phage. In another embodiment, the recombinant library is produced in M13 bacteriophage. In another embodiment, the recombinant viruses of the methods comprise peptides with mutations that abrogate binding to target of interest. In another embodiment, the receptor or enzyme of interest is not bound to a solid support. In another embodiment, the isolated viruses which have not infected cells, either after the step of introducing the receptor or enzyme of interest attached to a protease or after the step of introducing the protein (downstream signal transducer or enzyme substrate) attached to a protease or both, are attached to the surface of the cells, but have not entered said cells.

This invention is also directed to a composition which can be useful in the screening of drug candidates. In one embodiment of the invention, this invention provides a composition comprising: a recombinant virus peptide library made in accordance with the embodiments of the present invention and a target of interest connected to a protease.

With this assay, one can screen a collection of peptides for the one that exhibits the most desired characteristic. For example, the peptide that is most efficacious in activating the target of interest may be selected. Alternatively, the peptide that is most efficacious in blocking, inhibiting or competing with a ligand, which binds and activates the target of interest, may be selected.

In one embodiment, an advantage to the present methodology may comprise functional selection, which is an inherent part of the assay, saving cumbersome and time-consuming screenings at later stages. In another embodiment, sporadic deletion mutants that occur in the selection process using conventional techniques are avoided in the technology of the present invention. In another embodiment, non-specific binding problems resulting from tagging targets to a solid matrix are avoided, because a solid support is not necessary for the technology. In another embodiment, transient interactions, such as enzymes with their substrates can be detected by this technology. Finally, in another embodiment, this invention allows superior detection of proteins with either low- or high-affinity binding to a target of interest.

It should be likewise be apparent that the function of the polypeptides can be identified, i.e. this invention enables, in one embodiment, to determine whether the polypeptide can block the action of a toxin or whether it has an enhancing or an inhibiting effect on other processes such as cellular, biochemical, or physiological processes, such as cellular signal transduction, transcriptional regulation, translational regulation, cell adhesion, migration or transport, cytokine secretion and other aspects of the immune response, and the like.

In one embodiment, the peptides identified by the present invention may be used for diagnosis of a disease or for treating a disorder characterized by an absence of, inappropriate, or unwanted expression of the protein. Accordingly, methods for treatment include the use of the identified protein or fragments thereof. In another embodiment, the peptides identified by the present invention may be used to identify a person who is vulnerable to or has a proliferative disorder, which in one embodiment, is a cancer. In another embodiment, may be used to identify a person who is vulnerable to or has an infection, in another embodiment, an HIV infection, in another embodiment, a developmental disorder, while in another embodiment, a metabolic disorder. In another embodiment, peptides identified by the present invention may be used to treat a person with cancer. In another embodiment, peptides identified by the present invention may be used to treat a person with a proliferative disorder, an infection, an HIV infection, a developmental disorder, or a metabolic disorder. In another embodiment, it may be used to suppress, inhibit, or prevent any of the disorders mentioned hereinabove.

SoAP Assay Containing a Sterically Inhibiting Group

In another embodiment, this invention provides a second recombinant virus comprising: at least one protein or protein fragment, comprising segments which are involved in a vital process; a peptide or polypeptide which differs by at least one amino acid from another peptide or polypeptide in said library; a modified cleavage site proximal to said peptide and to said protein; and a sterically inhibiting group, wherein said sterically inhibiting group inhibits the function of said protein essential for a vital process.

The invention also provides a second library comprising such recombinant viruses.

In one embodiment, this invention provides a replicable genetic package peptide library, such as a second recombinant virus library, for identifying potential new drug candidates and lead compounds. In another embodiment, the invention provides methods for identifying the agonistic or antagonistic features of a peptide identified as having an intermolecular interaction with a target of interest. In another embodiment, this invention provides compositions, which can serve in an assay kit, for screening peptides for their ability to bind to a target of interest. In another embodiment, this invention provides compositions for screening peptides for their agonistic or antagonistic features.

In one embodiment, the sterically inhibiting group comprises a selectable marker. The selectable marker can be any selectable marker, which is known in the art, such as antibiotic resistance protein, for example, without being limited, ampicillin. The selectable marker can be also used for deletion mutants counter selection, when there is a need to select cells that are infected by virus that did not lose essential genes. In another embodiment, the protein essential for vital cellular process is a protein required for survival, infectivity or propagation. In another embodiment, the modified cleavage site is inserted between said peptide and said at least one protein essential for infectivity or propagation.

In one embodiment, the present invention provides a replicable genetic package peptide library wherein each replicable genetic package comprises at least one protein or protein fragment, which is involved in a vital process; a peptide or polypeptide, which differs by at least one amino acid from another peptide or polypeptide in said library; a modified cleavage site proximal to said peptide and to said protein; and a sterically inhibiting group, wherein said sterically inhibiting group inhibits the function of said protein essential for a vital process.

The invention also provides a library of such replicable genetic packages.

In one embodiment, the selectable marker is a part of the sterically inhibiting group. In another embodiment, the selectable marker is an antibiotic resistance gene. In another embodiment, the protein essential for vital cellular process is a protein required for survival, infectivity or propagation. In another embodiment, the modified cleavage site is inserted between said peptide and said at least one protein essential for infectivity or propagation.

In another embodiment, the genetic package is for example, without limitation, eukaryotic cell, bacteria, a virus, or a phage.

In one embodiment, the present invention provides a method of identifying a peptide having intermolecular interaction with a target of interest comprising the steps of: (a) introducing a target of interest attached to a protease to said second recombinant virus library of claim 1; (b) contacting said second recombinant virus library with cells; and (c) detecting viruses that are propagating, wherein if a cell comprises a recombinant virus which contain a peptide that has affinity to the target of interest, the sterically inhibiting group will be cleaved off and the virus will propagate.

In one embodiment, said peptide is an agonist, an antagonist, an antigen, an enzyme activating substrate, an inhibitor, a DNA or RNA binding peptide, transcription or translation activator or repressor. In another embodiment, the target of interest is a receptor, an antibody, a carrier, an information protein, a hormone, a regulatory protein, a structural protein, a toxin, an enzyme, DNA, RNA, oligonucleotide, synthetic or physiological polymer or a small organic molecule. In another embodiment, said peptide is used for epitope mapping of the target of interest. In another embodiment, the recombinant virus library is in M13 bacteriophage. In another embodiment, the protein essential for infectivity or propagation is pIII. In another embodiment, the target of interest is not bound to a solid support.

In one embodiment, there is provided a method of identifying a peptide having an intermolecular interaction with a target of interest comprising the steps of: preparing a second recombinant virus library according to an embodiment of the invention, wherein at least portion of the second recombinant virus is inactivated by the sterically inhibiting group attached to a protein essential for a vital process, and the inactivation can be reverted upon the removal of the sterically inhibiting group; introducing a target of interest, which is attached to a protease to said second recombinant virus library; the cell culture will be enriched with cells infected by a second recombinant virus which comprises a peptide that has affinity to the target of interest, due to the removal of the sterically inhibiting group, and the second virus will propagate.

The method is based on the concept that only when the target of interest interacts with a peptide, the susceptibility of the modified protease site to proteolysis is reverted, and the sterically inhibiting group is removed and enables the protein which is essential to a vital process to function. It should be noted in this respect that the level of the proteolytic activity is dependent on the affinity between the target protein and the peptide of the second library which is attached to the modified protease site. The methods of the invention are not limited to one cycle. Rather, in one embodiment, the method is performed with one cycle. In another embodiment, the method is performed with two cycles. In another embodiment, the method is performed with three cycles. In another embodiment, the method is performed with four cycles. In another embodiment, the method is performed with five cycles. In another embodiment, the method is performed with seven cycles. In another embodiment, the method is performed with nine cycles.

In one embodiment, the present invention provides a method of identifying a peptide or polypeptide, which has intermolecular interaction with a target of interest comprising the steps of: introducing a target of interest contacted to a protease to said replicable genetic package of claim 6; and detecting the replicable genetic package which propagates or survives, wherein only if the replicable genetic package contains a peptide that has affinity to the target of interest, the sterically inhibiting group will be cleaved off and the replicable genetic package will be able to propagate or survive.

In one embodiment, said peptide is an agonist, an antagonist, an antigen, an enzyme activating substrate, an inhibitor, a DNA or RNA binding peptide, transcription or translation activator or repressor. In another embodiment, the target of interest is a receptor, an antibody, a carrier, an information protein, a hormone, a regulatory protein, a structural protein, a toxin or an enzyme, a DNA, an RNA, an oligonucleotide, a synthetic polymer or a small organic molecule. In another embodiment, said replicable genetic package is a eukaryotic cell, bacteria, a virus, or a phage. In another embodiment, the target of interest is not bound to a solid support.

In one embodiment, the present invention provides a composition for identifying a peptide that has intermolecular interaction with a target of interest comprising: the second recombinant virus peptide library described above; and a target of interest connected to a protease.

In one embodiment, the present invention provides a composition for identifying a peptide that has intermolecular interaction with a target of interest comprising: a replicable genetic package peptide library as described hereinabove and a target of interest connected to a protease.

In one embodiment, the present invention provides a peptide or polypeptide, which has an intermolecular interaction with a target of interest, isolated according to any of the methods described herein.

It should likewise be apparent that a wide range of polypeptides that have a function i.e. have an agonistic or an antagonistic effect on the target of interest of the invention, can be identified by the process of the invention. In one embodiment, the present invention provides a method of identifying an agonistic or antagonistic feature of a peptide, which has intermolecular interaction with a receptor of interest comprising the steps of: (a) contacting a receptor of interest connected to a protease, to said second recombinant virus library as described hereinabove; (b) contacting said second recombinant virus library with cells; (c) detecting the propagated viruses, wherein if a cell comprises a recombinant virus which comprises a peptide that has affinity to the to the target of interest the sterically inhibiting group will be cleaved off and the virus will propagate; (d) contacting the propagated viruses of step c with the receptor of interest; (e) contacting the viruses of step d with a protein attached to protease, wherein said protein is downstream in the signal transduction pathway of the receptor of interest; (f) contacting the viruses of step e with cells; and (g) separating the cells obtained in step f, so as to obtain infected cells and non infecting viruses, wherein if a virus infects a cell, it contains a peptide which has an agonistic feature and if a virus is a non infecting virus it contains a peptide which has an antagonistic feature, thereby identifying an agonistic or antagonistic feature of a peptide, which has intermolecular interaction with a receptor of interest.

In one embodiment, the present invention provides a method of identifying peptide which has a functional feature with a receptor of interest comprising the steps of: (a) contacting a receptor of interest connected to a protease, to the second recombinant virus peptide library as described hereinabove; (b) contacting said second recombinant virus library with cells; (c) detecting the propagated viruses, wherein if a cell comprises a second recombinant virus which comprises a peptide that has affinity to the target of interest, the sterically inhibiting group will cleave off enabling the virus propagation; (d) contacting the propagated viruses of step c with said receptor of interest; (e) contacting the viruses of step d with a ligand to the receptor of interest attached to the protease; (f) contacting the viruses of step e with host cells; and (g) separating the infected cells and the non infecting viruses obtain in step f, so as to obtain infected cells and non infecting viruses, wherein if a virus infects a cell, it contains a peptide which does not have functional feature and if the virus is a non infecting virus it contains a peptide which has a functional feature, thereby identifying a peptide which has a functional feature with a receptor of interest.

In one embodiment, the term "functional feature" refers hereinbelow to any function that the peptide might produce on the receptor of interest, namely agonistic reaction or antagonistic reaction.

In one embodiment, the present invention provides a method of identifying peptide that inhibits an enzyme of interest comprising the steps of: (a) contacting an enzyme of interest connected to a protease, to the second recombinant virus peptide library as described hereinabove; (b) contacting said second recombinant virus library with cells; (c) detecting the propagated viruses, wherein if a cell comprises a second recombinant virus, which comprises a peptide that has affinity to the enzyme of interest, the sterically inhibiting group will cleave off enabling the virus propagation; (d) contacting the viruses of step c with said enzyme of interest; (e) contacting the viruses of step d with a substrate of the enzyme, wherein said substrate is attached to a protease; (f) contacting the viruses of claim e with cells; and (g) separating said cells by spinning down or filtration, so as to obtain infected cells in the pellet or and non infecting viruses which contain a peptide which inhibits an enzyme inhibiting peptide in the supernatant; thereby identifying peptide which inhibits an enzyme of interest.

In one embodiment, the present invention provides a method of identifying a peptide that activates an enzyme of interest comprising the steps of: (a) contacting an enzyme of interest connected to a protease, to the second recombinant virus peptide library as described hereinabove; (b) contacting said second recombinant virus library with cells; (c) detecting the propagated viruses, wherein if a cell comprises a second recombinant virus, which comprises a peptide that has affinity to the enzyme of interest, the sterically inhibiting group will cleave off enabling the virus propagation; (d) contacting the viruses propagated in step c with said enzyme of interest; (e) contacting the viruses of step d with a substrate of the enzyme, wherein said substrate is attached to a protease; (f) contacting the viruses of claim e with cells; (g) detecting the propagated viruses, wherein if a cell comprises a recombinant virus, the virus comprises a peptide which activates the enzyme of interest, the sterically inhibiting group will cleave off enabling the virus propagation; and (h) separating the non infecting viruses from infected cells, thereby obtaining enriched population of peptides which activates an enzyme of interest.

The methods of identification the function of the identified peptide, its agonistic or antagonistic property, or whether it activates or inhibits an enzyme are not limited to second recombinant virus libraries. The methods may be applied in any replicable genetic packages. In one embodiment, the present invention provides a method of identifying an agonistic or antagonistic feature of a peptide, which has intermolecular interaction with a receptor of interest comprising the steps of: (a) contacting a receptor of interest connected to a protease, to said replicable genetic package as described hereinabove; (b) detecting the replicable genetic package which propagate or survive, wherein if a replicable genetic package comprises peptide that has affinity to the to the target of interest, the sterically inhibiting group will be cleave off and the replicable genetic package will propagate or survival; (c) contacting the replicable genetic package of step b with the receptor of interest; (d) contacting the replicable genetic package of step d with a protein attached to protease, wherein said protein is downstream in the signal transduction pathway of the receptor of interest; and (e) separating the replicable genetic package obtained in step d, wherein if a replicable genetic package propagates or survives, it contains a peptide which has an agonistic feature.

In one embodiment, the present invention provides a method of identifying peptide which has a functional feature with a receptor of interest comprising the steps of: (a) contacting a receptor of interest connected to a protease, to the replicable genetic package as described hereinabove; (b) detecting the replicable genetic package which propagate or survive, wherein if a replicable genetic package comprises a peptide that has affinity to the target of interest the sterically inhibiting group will cleaved off enabling the replicable genetic package propagation or survive; (c) contacting the replicable genetic package of step b with a ligand to the receptor of interest attached to the protease; and (d) separating the replicable genetic package which survive or propagate, thereby identifying a peptide which has a functional feature with a receptor of interest.

In one embodiment, the present invention provides a method of identifying a peptide that activates an enzyme of interest comprising the steps of: (a) contacting an enzyme of interest connected to a protease, to the replicable genetic package as described hereinabove; (b) detecting the replicable genetic package which survives or propagates, wherein if a replicable genetic package comprises a peptide that has affinity to the enzyme of interest, the sterically inhibiting group was cleave off enabling the virus propagation; (c) contacting the replicable genetic package of step b with said enzyme of interest; (d) contacting the replicable genetic package of step c with a substrate of the enzyme, wherein said substrate is attached to a protease; and (e) detecting the replicable genetic package which survives or propagates, wherein if said replicable genetic package comprises a peptide that activates the enzyme of interest, the inhibiting group is cleaved off enabling the replicable genetic package propagation; thereby identifying a peptide which activates an enzyme of interest.

The concept of this embodiment of the invention is to attach a sterically inhibiting group, which comprises a modified protease cleavage site and a peptide library to a protein which is essential to any vital process of any organism so as to inhibit a function of the essential protein. The modified organism is then contacted with a target of interest attached to a protease. Only when the target of interest has affinity to a peptide of the peptide library, the sterically inhibiting group will be cleaved off and the function of the protein, which is essential to a vital process, will be reverted.

In one embodiment, the peptide and modified protease site, which are attached to the protein that is essential to a vital process, form a sterically inhibiting group.

By the word “sterically inhibiting group” or “steric hindrance” it is meant interference with a feasible chemical reaction. Here it means physical inhibition of the protein function by attaching a chemical group to a protein, which protein is essential for a vital process.

The virus library may utilize a number of expression vehicles known to those of ordinary skill, including but not limited to, recombinant bacteriophage, lambda phage, M13, a recombinant plasmid or cosmid, and the like. If the virus used is M13, the protein, which is essential for propagation and infectivity, may be without limitation, pIII or pVIII and the like. Accordingly, the M13 cannot be infective when a sterically inhibiting group is attached for example, to the N terminus of pIII and would be activated only upon the removal of the sterically inhibiting group by, for example, a suitable protease.

A prophetic example which demonstrates the concept of the invention is the use of auxotrophic bacteria. An auxotrophic bacterium is a mutant bacterium that requires nutrients that wild type bacteria are able to synthesize themselves. For example, an arginine mutant requires a nutritional supplement of arginine in order to grow, because it lacks the enzyme responsible for arginine production. Any of the methods of the present invention may use auxotrophic bacteria, in which the missing enzyme is expressed in a plasmid, fused to a sterically inhibiting group that comprises peptide library, a modified protease site, and optionally an antibiotic resistance protein (for the deletion mutants counter selection), wherein the sterically inhibiting group inhibits the activity of the enzyme. These bacteria can grow only on rich media. Growing the bacteria on minimal medium will select for the bacterial cells expressing peptide that interact with the target of interest, because the sterically inhibiting group in these cells will be preferably cleaved off, and the enzyme will revert its full activity. It should be noted that the rate of the bacteria growth will be dependent on the interaction of the target with the peptide.

In another embodiment, the method can be performed with cells that can grow in a medium containing a specific antibiotic and express the antibiotic resistance gene fused to the sterically inhibiting group. The antibiotic resistance gene will be activated only when the sterically inhibiting group will be removed and the cells will be able than to propagate. The cells may be further containing an antibiotic resistance gene for the deletion mutants counter selection.

EXAMPLES

M13, as well as fd and f1, is a filamentous Ff bacteriophage. The phage minor coat gene 3 protein (pIII) of M13 bacteriophage (FIG. 1A) allows the phage to infect bacteria by interacting with the bacterial F pilus and later with the integral membrane protein TolA. Specifically, the CT domain of pIII anchors pIII to the phage coat, while the N2 domain interacts with bacterial F pilus and the N1 domain forms a complex with the C-terminal of TolA at later stages of infection.

One of skill in the art would be well equipped to construct a vector through standard recombinant techniques (see, for example, Maniatis, et al., Molecular Cloning, A laboratory Manual (Cold Spring Harbor, 1990) and Ausubel, et al., 1994, Current Protocols In Molecular Biology (John Wiley & Sons, 1996), both incorporated herein by reference).

Example 1

Development of a Recombinant Virus Library with a Modified Protease Site

M13 is only active (i.e. able to infect) when the N2 and N1 domains are tightly linked to the CT domain, which is linked to the capsid of the phage. In addition, a phage remains active if any one of its 3-5 pIII units is functional. Thus, insertion of a protease cleavage site between the CT and the N2 domains of pIII would render the phage inactive (FIG. 1B) upon incubation with a suitable amount and type of protease.

In order to develop a system in which interaction of heterologous proteins may be assessed, a protease and protease cleavage site pair is chosen, wherein cleavage will only occur if the protease and the protease cleavage site are brought into close proximity by another group (FIG. 2). Thus, an appropriate modified protease cleavage site of the pair should have minimal affinity for its protease but at the same time, should sustain high proteolytic activity when it comes into contact with its protease. Thus, if the protease described above is fused to a target protein and the protease cleavage site in the pIII protein is cross-linked to a target protein ligand, the specific proteolytic activity of the protease will be activated by bringing the protease and protease cleavage site into close proximity (FIG. 2). A higher affinity of the target protein to the target protein ligand would be expected to increase the proteolytic activity.

Each of the recombinant proteins in the system, such as the protease-target protein and the modified cleavage site-target protein ligand, are separated by long flexible linkers to enable a good degree of rotational freedom, which in turn allows interaction between the components of the system. The linkers chosen may include a leucine zipper. Any other flexible linker could be used as well.

Figure 3:
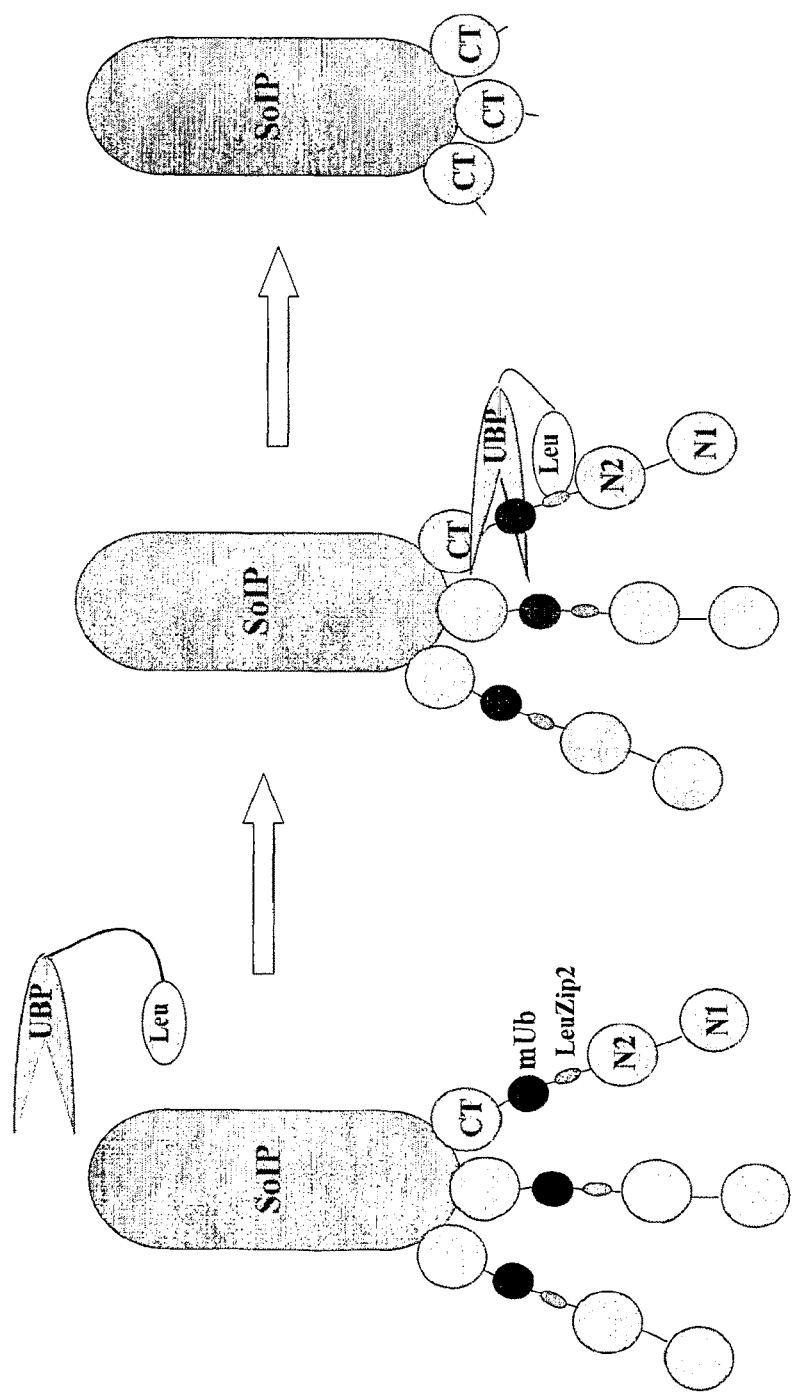
FIG. 3 is an illustration of a preferred embodiment of a SoIP, specifying the identity of the modified protease site. SoIP comprises the pIII domains of wild type bacteriophage, but with an insertion of a modified ubiquitin sequence (mUb) and one half of a leucine zipper peptide (LeuZip2) between the N2 and CT domains of each pIII protein. Cleavage of the N1 and N2 domains of pIII occurs in SoIP when the second half of a leucine zipper peptide (LeuZip1), which is fused to a UBP protease, binds to LeuZip2 expressed on the pIII protein. The resultant proximity of UBP to mUb results in proteolysis of N1, N2, LeuZip2, and mUb from the CT domain of pIII and the capsid.

The 76 amino acid-long ubiquitin proteolytic site (Genbank X01474; PID: g4741) and one of ubiquitin's specific proteases, UBP1 (Genbank M63484; PID: g173126) are identified as suitable candidates for modified cleavage site and protease, respectively (FIG. 3). UBP1 specifically cleaves ubiquitin after its C-terminal glycine. A modified ubiquitin structure that is bound by UBP1 with very low or no affinity but has a preserved UBP1 cleavage site is generated using a mutagenesis library of ubiquitin generated by PCR.

Example 2

Testing of a Recombinant Virus Library with a Modified Ubiquitin Site

The two parts of a leucine-zipper are used to evaluate the functionality of the modified ubiquitin system in the present invention (FIG. 3). The protease cleavage site is cross-linked to one part of the leucine zipper, and the protease is engineered as a fusion protein with another part of the leucine zipper. When combined, the two parts of the leucine zipper interact, resulting in the association of the UBP1 with modified ubiquitin. Any other two interacting molecules could be used, but they should preferably be small and have a strong affinity for one another.

Engineered and wild type bacteriophages are incubated with and without the target ligand fusion protein. After incubation of the phages with the fusion protein, bacteria are added to the medium. After incubation of the phages with bacteria, bacteria are removed from the medium to separate bacteriophages in the medium from those that invaded the bacterial host cell (FIG. 4). Bacteria are then washed and resuspended in water. The genomes of the inactive phages that are not able to infect the bacterial cells are rescued from the filtrate by PCR. Alternatively, the genomes of the active phages from the bacterial cells are rescued by PCR.

Wild type bacteriophages and engineered bacteriophages that were not exposed to the target protein ligand are found in high levels in the host bacteria. However, bacteriophages engineered with the leucine zipper construct cross-linked to the modified ubiquitin described above are found in high levels in the incubation medium, indicating that the pIII protein was cleaved and the phage thus rendered non-infective. Thus, in the engineered bacteriophage system described hereinabove, the inability of a phage to invade a host cell indicates the presence of a protein-protein interaction.

Example 3

SoIP Assay to Identify Peptide that Interacts with a Target of Interest

Figure 5A:
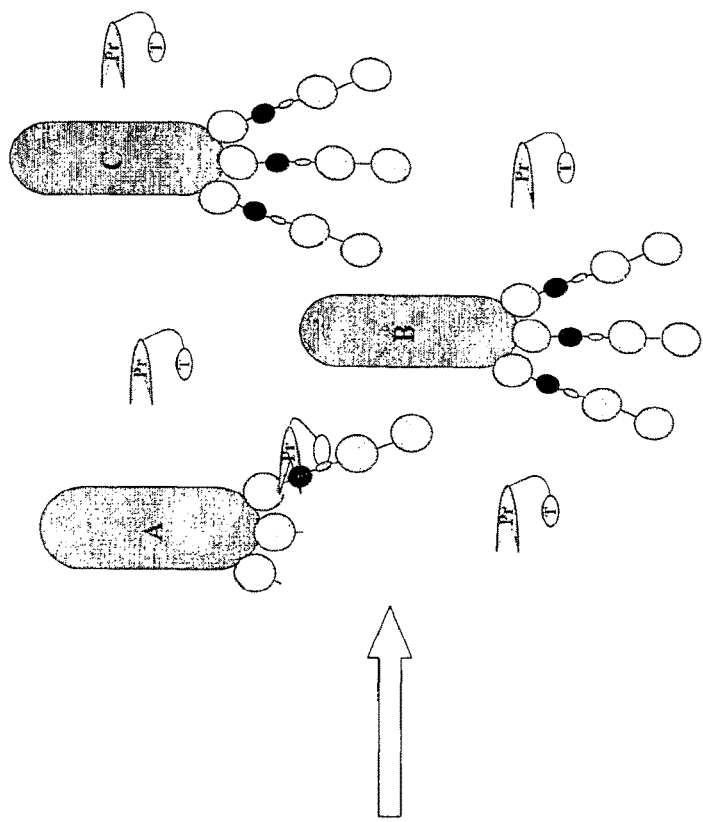
FIGS. 5A-D are an illustration in one embodiment of the method of identifying proteins that interact with a protein of interest. A recombinant virus library, in which each recombinant virus expresses a peptide unique from those expressed by other recombinant viruses in the library, is incubated with a fusion protein comprising a known target peptide or polypeptide fused to a protease via a flexible linker. Library peptides with an affinity for the target will be cleaved. The library is then incubated with cells. Recombinant viruses with cleaved pIII proteins will be unable to infect cells.
Figure 5B:
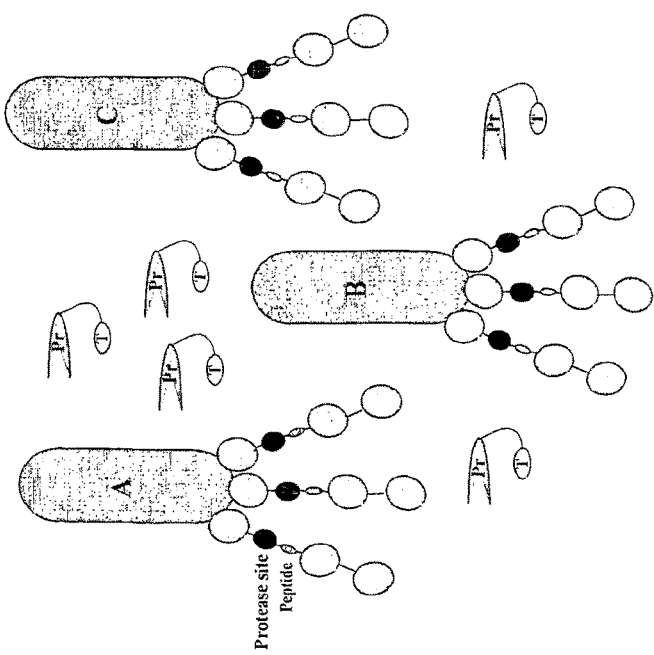

Next, a library of M13 bacteriophages is created which contain an insertion of the modified protease cleavage site (ubiquitin) and a random peptide between the CT and N2 domains of pIII (FIG. 2, 5A). The target protein is fused to one half of a leucine zipper, and a protease (UBP1) is fused to a second half of a leucine zipper. The target protein and UBP1 are then cross-linked by the leucine zipper (FIG. 2, 5A), creating a complex comprising the target of interest. After incubation of the M13 library with the target fusion protein (FIG. 5A-B), bacteria are added to the medium (FIG.

Figure 5D:
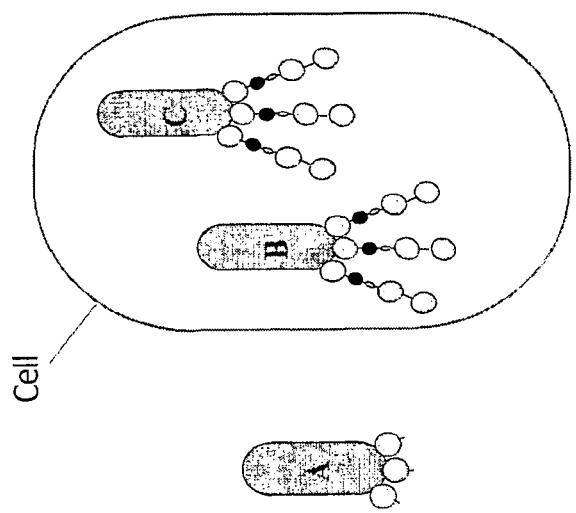
Figure 5C:
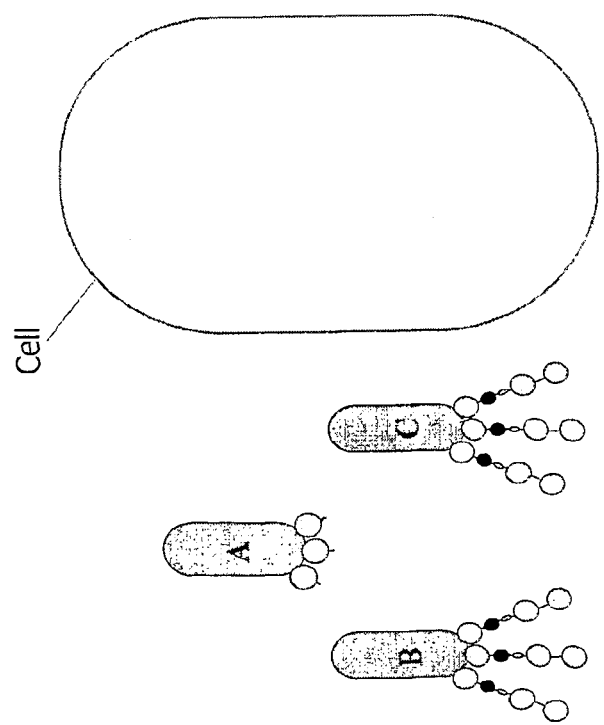

5C). After an appropriate incubation (FIG. 5D), bacteria are separated from the medium, and the genomes of the active and inactive phages are separated, recovered, and sequenced as described hereinabove.

Bacteriophages that successfully invade the bacterial host cell are expected have at least one intact pIII protein, indicating that the target protein and target protein ligand did not have a high affinity (FIG. 4). Bacteriophage in the medium are expected to be missing all of their pIII proteins, indicating that the target protein and target protein ligand displayed high affinity binding (FIG. 4). In this way, novel targets of a characterized protein can be isolated from libraries.

Example 4

SoIP Assay to Identify a Functional Interaction Between Peptide and Target of Interest The positive or negative functionality of novel targets of a characterized protein may be characterized using the method described herein.

In the case where the target of interest is a receptor, the first step is to perform the technique described Example 3 to screen a peptide library for a peptide that interacts with a receptor protein whose downstream signaling molecule is characterized. Then, clones of cells that were non-infective in Example 3 are incubated with a receptor protein that is not fused to a protease (UBP1). Next, the protease (UBP1) is engineered as a fusion protein with a protein known to be involved in the downstream signaling of the target (FIG. 6B). After incubation of the recombinant virus library with the known signaling molecule fusion protein, bacteria are added to the medium. After an appropriate incubation, bacteria are separated from the medium, and the genomes of the active and inactive phages are separated and recovered as described hereinabove.

If the peptide expressed by the recombinant bacteriophage is an antagonist of the receptor of interest, then it will bind the receptor of interest and prevent an interaction of the receptor with its downstream protein. Thus, there will be no opportunity for interaction between the protease and modified cleavage site, because the downstream protein, which is linked to a protease, will not interact with the receptor of interest and the peptide, which are in close proximity to the modified cleavage site. Thus, the pIII protein of the bacteriophage will remain intact, along with the ability of the phage to infect (FIG. 6D). Thus, bacteriophage localized in cells express peptides that are antagonistic with respect to the receptor of interest.

If the peptide expressed by the recombinant bacteriophage is an agonist of the receptor of interest, then it will bind the receptor of interest and lead to an interaction of the activated receptor with its downstream protein. The proximity of the downstream protein, which is linked to a protease, to the receptor of interest and the peptide, which are in close proximity to the modified cleavage site, will lead to the cleavage of the cleavage site by the protease, the loss of the pIII protein, and the loss of ability to infect (FIG. 6C). Thus, bacteriophage in the medium express peptides that are agonistic with respect to the receptor of interest.

A second illustration of the assay's ability to exhibit functionality of a peptide is the case where the target of interest is an enzyme. The first step is to perform the technique described Example 3 to screen a peptide library for a peptide or peptides that interact with an enzyme whose substrate is characterized. Then, clones of cells that were non-infective in Example 3 are incubated with an enzyme that is not fused to a protease (UBP1). Next, the protease (UBP1) is engineered as a fusion protein with the enzyme substrate (FIG. 6B). After incubation of the recombinant virus library with the known enzyme substrate fusion protein, bacteria are added to the medium. After an appropriate incubation, bacteria are separated from the medium, and the genomes of the active and inactive phages are separated and recovered as described hereinabove.

If the peptide expressed by the recombinant bacteriophage is an inhibitor of the enzyme of interest, then it will bind the enzyme of interest and prevent an interaction of the enzyme with its substrate. Thus, there will be no opportunity for interaction between the protease and modified cleavage site, because the enzyme substrate, which is linked to a protease, will not interact with the enzyme of interest and the peptide, which are in close proximity to the modified cleavage site. Thus, the pIII protein of the bacteriophage will remain intact, along with the ability of the phage to infect (FIG. 6D). Thus, bacteriophage localized in cells express peptides that are inhibitors of the enzyme of interest.

If the peptide expressed by the recombinant bacteriophage is an activator of the enzyme of interest, then it will bind the enzyme of interest and lead to an interaction of the activated enzyme with its substrate. The proximity of the substrate, which is linked to a protease, to the enzyme of interest and the peptide, which are in close proximity to the modified cleavage site, will lead to the cleavage of the cleavage site by the protease, the loss of the pIII protein, and the loss of ability to infect (FIG. 6C). Thus, bacteriophage in the medium express peptides that are activators of the enzyme of interest. In this way, the way in which the novel peptide affects characterized target-ligand interactions may be assessed.

What is claimed is:

1. A system comprising a recombinant bacteriophage library and a target of interest complex, wherein the recombinant bacteriophage peptide library comprises a plurality of peptides expressed on the surface of recombinant bacteriophages wherein each recombinant bacteriophage comprises:
   (a) a pIII protein; wherein each pIII protein comprises:
   (b) a peptide or polypeptide involved in an intermolecular interaction, which differs by at least one amino acid from other peptides or polypeptides in said library; and
   (c) a modified protease cleavage site proximal to said peptide, wherein said modified protease cleavage site is the same in each bacteriophage, said modified cleavage site having a reduced binding affinity to a protease, as compared to a non-modified cleavage site, and wherein the target of interest complex comprises a protease, a flexible linker attached to said protease, and a target of interest attached to said flexible linker, wherein said target of interest participates in an intermolecular interaction.

2. The system of claim 1, wherein the target of interest is an agonist, antagonist, receptor, antibody, antigen, enzyme, enzyme activator, enzyme inhibitor, enzyme substrate, hormone, regulatory protein, cytoskeletal protein, toxin, synthetic or physiological polymer, small organic molecule, DNA, RNA, oligonucleotide, transcriptional activator or repressor, translational activator or repressor, or a functional fragment thereof.

3. The system of claim 2, wherein said target of interest is other than a protease.

4. The system of claim 1, wherein the flexible linker is at least 3 amino acids in length.

5. A kit for identifying a peptide or polypeptide involved in an intermolecular interaction with a target of interest comprising:
   (a) a recombinant bacteriophage peptide library comprising a plurality of peptides expressed on the surface of recombinant bacteriophages wherein each recombinant bacteriophage comprises:
      a pIII protein; wherein each pIII protein comprises:
      a peptide or polypeptide involved in an intermolecular interaction, which differs by at least one amino acid from other peptides or polypeptides in said library; and
      a modified protease cleavage site proximal to said peptide, wherein said modified protease cleavage site is the same in each bacteriophage, said modified cleavage site having a reduced binding affinity to a protease, as compared to a non-modified cleavage site;
   (b) a target of interest attached to a protease via a flexible linker; and
   (c) cells that are susceptible to bacteriophage attachment, infection or a combination thereof.

6. The kit of claim 5, wherein said peptide or polypeptide is an agonist, antagonist, antigen, enzyme, enzyme activator, enzyme inhibitor, enzyme substrate, other than a protease cleavage site, hormone, regulatory protein, cytoskeletal protein, toxin, transcriptional activator or repressor, translational activator or repressor, or a functional fragment thereof.

7. The kit of claim 5, wherein said target of interest is other than a protease.

8. The kit of claim 5, wherein the flexible linker is at least 3 amino acids in length.

* * * * *

UNITED STATES PATENT AND TRADEMARK OFFICE
CERTIFICATE OF CORRECTION

PATENT NO. : 10,160,967 B2
APPLICATION NO. : 14/923855
DATED : December 25, 2018
INVENTOR(S) : Morad et al.

It is certified that error appears in the above-identified patent and that said Letters Patent is hereby corrected as shown below:

On the Title Page

Item (57) ABSTRACT:
Line 5, after "recombinant bacteriophage includes (a) a", delete "pill" and insert -- pIII --.
Line 6, after "wherein each", delete "pill" and insert -- pIII --.

Signed and Sealed this
Twelfth Day of February, 2019

Andrei Iancu
*Director of the United States Patent and Trademark Office*

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: flexible linker

<400> SEQUENCE: 1

Gly Gly Gly Ser
1